(12) United States Patent
Cordingley et al.

(10) Patent No.: US 8,557,840 B2
(45) Date of Patent: Oct. 15, 2013

(54) HERBICIDAL COMPOUNDS

(75) Inventors: Matthew Robert Cordingley, Bracknell (GB); Michael Drysdale Turnbull, Bracknell (GB); Nigel James Willetts, Bracknell (GB); Patrick Jelf Crowley, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 424 days.

(21) Appl. No.: 12/863,282

(22) PCT Filed: Jan. 16, 2009

(86) PCT No.: PCT/GB2009/000126
§ 371 (c)(1),
(2), (4) Date: Oct. 13, 2010

(87) PCT Pub. No.: WO2009/090401
PCT Pub. Date: Jul. 23, 2009

(65) Prior Publication Data
US 2011/0034334 A1    Feb. 10, 2011

(30) Foreign Application Priority Data
Jan. 17, 2008    (GB) .................................... 0800855.9

(51) Int. Cl.
*A01N 43/42* (2006.01)
*A61K 31/44* (2006.01)

(52) U.S. Cl.
USPC ........................................................ 514/300

(58) Field of Classification Search
USPC ............................ 546/122; 504/246; 514/300
See application file for complete search history.

(56) References Cited

U.S. PATENT DOCUMENTS

| 2004/0087577 A1 | 5/2004 | Pratt et al. |
| 2006/0040927 A1 | 2/2006 | Blake et al. |

FOREIGN PATENT DOCUMENTS

| EP | 0500297 A1 | 8/1992 |
| EP | 0537463 A2 | 4/1993 |
| WO | 9530676 | 11/1995 |
| WO | 03/010145 | 2/2003 |
| WO | 03059356 A2 | 7/2003 |
| WO | 2004018419 A2 | 3/2004 |
| WO | 2004041818 A1 | 5/2004 |
| WO | 2004/056825 | 7/2004 |
| WO | 2004056829 A1 | 7/2004 |
| WO | 2005010000 | * 2/2005 |
| WO | 2005047244 A2 | 5/2005 |
| WO | 2005/123733 | 12/2005 |

OTHER PUBLICATIONS

CAS Abstract No. XP002578002 retrieved from STN Database Accession No. 145:167218.
CAS Abstract No. XP002578003 retrieved from STN Database Accession No. 64:43760.

* cited by examiner

*Primary Examiner* — Niloofar Rahmani
(74) *Attorney, Agent, or Firm* — James Cueva

(57) ABSTRACT

The present invention relates to a method of controlling plants or inhibiting plant growth which comprises applying to the plants or to the locus thereof a herbicidally effective amount of a compound of formula (I): wherein $A^1, A^2, A^3, A^4, R^3, R^4$ and $R^5$ are as defined in claim 1; or a salt or N-oxide thereof. Furthermore, the present invention relates to processes for preparing compounds of formula (I), to intermediates used in the preparation of compounds of formula (I), to herbicidal compositions comprising compounds of formula (I) and to certain novel pyridopyridines, pyridodiazines and pyridotriazines.

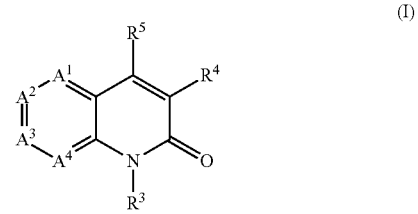

5 Claims, No Drawings

HERBICIDAL COMPOUNDS

This application is a 371 of International Application No. PCT/GB2009/000126 filed Jan. 16, 2009, which claims priority to GB 0800855.9 filed Jan. 17, 2008, the contents of which are incorporated herein by reference.

The present invention relates to novel herbicidal pyridopyridines, pyridodiazines and pyridotriazines, to processes for their preparation, to compositions comprising these compounds, and to their use in controlling plants or in inhibiting plant growth.

Certain pyridopyridines were disclosed as intermediates in the synthesis of fungicidal compounds, for example, in WO 04/056824. Certain pyridopyrimidines were disclosed as intermediates in the synthesis of fungicidal compounds, for example, in WO 04/056825 and WO 04/056826. Certain pyridotriazines were disclosed as intermediates in the synthesis of fungicidal compounds, for example, in WO 04/056829. Certain pyridopyridines and pyridopyrimidines were disclosed as fungicidal compounds, for example, in WO 05/010000. Certain pyridopyridines were disclosed as pharmaceutical compounds, for example, in WO 95/30676, JP 07053546 and WO 01/62252. Certain pyridodiazines and pyridotriazines were disclosed as pharmaceutical compounds, for example, in WO 02/076396. Certain pyridopyrimidines were disclosed as pharmaceutical compounds, for example, in WO 02/076946, WO 06/124490 and WO 07/044,813. Certain pyridopyridines and pyridopyrimidines were disclosed as pharmaceutical compounds, for example, in WO 96/22990, WO 02/018383, WO 03/066630 and WO 07/136,465. Certain pyridopyridines were disclosed in *Journal of Heterocyclic Chemistry* (1993), 30(4), 909-12 and *Bioorganic & Medicinal Chemistry* (2001), 9(8), 2061-2071.

It has now surprisingly been found that certain pyridopyridines, pyridodiazines and pyridotriazines display excellent herbicidal and growth-inhibiting properties.

The present invention therefore provides a method of controlling plants which comprises applying to the plants or to the locus thereof a herbicidally effective amount of a compound of formula (I)

(I)

wherein
$A^1$, $A^2$, $A^3$ and $A^4$ are independently C—$R^1$ or N, provided at least one of $A^1$, $A^2$, $A^3$ and $A^4$ is N, and provided that if $A^1$ and $A^4$ are both N, $A^2$ and $A^3$ are not both C—$R^1$;
each $R^1$ is independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;
$R^3$ is hydrogen, $C_1$-$C_{10}$alkyl, $C_1$-$C_4$haloalkyl, $C_2$-$C_{10}$alkenyl, $C_2$-$C_4$haloalkenyl, $C_2$-$C_{10}$alkynyl, $C_2$-$C_4$haloalkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different;
$R^4$ is aryl or aryl substituted by one to five $R^8$, which may be the same or different, or heteroaryl or heteroaryl substituted by one to four $R^8$, which may be the same or different;
$R^5$ is hydroxy or a group which can be metabolised to a hydroxy group;
each $R^6$, $R^7$ and $R^8$ is independently halo, cyano, nitro, $C_1$-$C_{10}$alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy-substituted by one to three $R^{13}$, which may be the same or different, heteroaryloxy- or heteroaryloxy-substituted by one to three $R^{13}$, which may be the same or different, arylthio- or arylthio-substituted by one to three $R^{13}$, which may be the same or different, or heteroarylthio- or heteroarylthio-substituted by one to three $R^{13}$, which may be the same or different; and
each $R^{13}$ is independently halo, cyano, nitro, $C_1$-$C_6$alkyl, $C_1$-$C_6$haloalkyl or $C_1$-$C_6$alkoxy; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

For example, a compound of formula (Ia), i.e. a compound of formula (I) wherein $R^3$ is hydrogen and $R^5$ is hydroxy, can be drawn in at least five tautomeric forms.

(Ia)

-continued

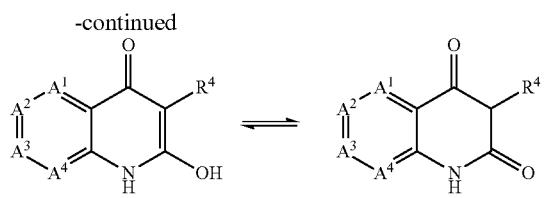

Some of these compounds exhibit good herbicidal activity. Additionally, these compounds can be used as intermediates for the synthesis of compounds of the formula (Ib), (Ic) and (Id).

For example, a compound of formula (Ib), i.e. a compound of formula (I) wherein $R^3$ is hydrogen and $R^5$ is as defined for compounds of formula (I) other than hydroxy, can be drawn in at least two tautomeric forms.

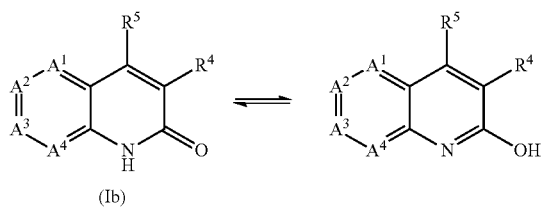

(Ib)

Some of these compounds exhibit good herbicidal activity. Additionally, these compounds can be used as intermediates for the synthesis of compounds of the formula (Ia), (Ic) and (Id).

A compound of formula (Ic), i.e. a compound of formula (I) wherein $R^3$ is as defined for compounds of formula (I) other than hydrogen and $R^5$ is as defined for compounds of formula (I) other than hydroxy, can be drawn in only one tautomeric form.

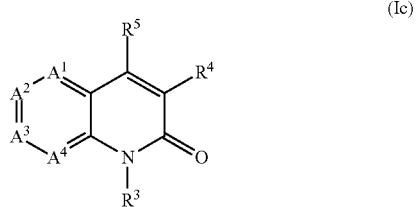

(Ic)

Most of these compounds exhibit excellent herbicidal activity. Additionally, these compounds can be used as intermediates for the synthesis of compounds of the formula (Ia), (Ib) and (Id).

A compound of formula (Id), i.e. a compound of formula (I) wherein $R^3$ is as defined for compounds of formula (I) other than hydrogen and $R^5$ is hydroxy, can be drawn in three tautomeric forms.

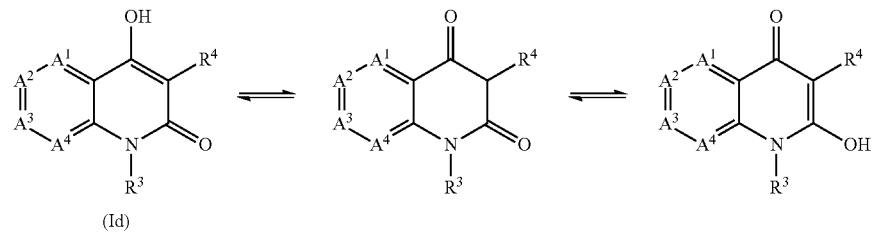

(Id)

Most of these compounds exhibit good herbicidal activity. Additionally, these compounds can be used as intermediates for the synthesis of compounds of the formula (Ia), (Ib) and (Ic).

Each alkyl moiety (either alone or as part of a larger group, such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$ to $C_6$ alkyl groups, more preferably $C_1$-$C_4$ and most preferably $C_1$-$C_3$ alkyl groups.

Alkenyl and alkynyl moieties (either alone or as part of a larger group, such as alkenyloxy or alkynyloxy) can be in the form of straight or branched chains, and the alkenyl moieties, where appropriate, can be of either the (E)- or (Z)-configuration. Examples are vinyl, allyl, prop-2-enyl and propargyl. The alkenyl and alkynyl groups are preferably $C_2$ to $C_6$ alkenyl or alkynyl groups, more preferably $C_2$-$C_4$ and most preferably $C_2$-$C_3$ alkenyl or alkynyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CHF_2$, —$CH_2CF_3$ or —$CH_2CHF_2$. Haloalkenyl and haloalkynyl groups (either alone or as part of a larger group, such as haloalkenyloxy or haloalkynyloxy) are alkenyl and alkynyl groups, respectively, which are substituted with one or more of the same or different halogen atoms and are, for example, —CH=$CF_2$, —CF=$CH_2$ or —C≡CCl.

Cyanoalkyl groups are alkyl groups which are substituted with one or more cyano groups, for example, cyanomethyl or 1,3-dicyanopropyl.

Cycloalkyl groups can be in mono- or bi-cyclic form and may optionally be substituted by one or more methyl groups. The cycloalkyl groups preferably contain 3 to 8 carbon atoms, more preferably 3 to 6 carbon atoms. Examples of monocyclic cycloalkyl groups are cyclopropyl, 1-methylcyclopropyl, 2-methylcyclopropyl, cyclobutyl, cyclopentyl and cyclohexyl.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings contain up to three and bicyclic systems up to four heteroatoms which are preferably chosen from nitrogen, oxygen and sulfur. Examples of monocyclic groups include pyridyl, pyridazinyl, pyrimidinyl, pyrazinyl, triazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. More preferred monocyclic groups are pyridyl, pyrimidinyl, thiophenyl, isoxazolyl, oxadiazolyl, and thiazolyl. Examples of bicyclic groups are benzothiophenyl, benzimidazolyl, benzothiadiazolyl, quinolinyl, isoquinolinyl, cinnolinyl, quinoxalinyl and pyrazolo[1,5-a]pyrimidinyl. More preferred bicyclic groups are quinolinyl and isoquinolinyl.

The term "heterocyclyl" is defined to include heteroaryl and in addition their unsaturated or partially unsaturated analogues such as 4,5,6,7-tetrahydro-benzothiophenyl, chromen-4-onyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

The term "herbicide" as used herein means a compound that controls or modifies the growth of plants. The term "herbicidally effective amount" means the quantity of such a compound or combination of such compounds that is capable of producing a controlling or modifying effect on the growth of plants. Controlling or modifying effects include all deviation from natural development, for example: killing, retardation, leaf burn, albinism, dwarfing and the like. The term "plants" refers to all physical parts of a plant, including seeds, seedlings, saplings, roots, tubers, stems, stalks, foliage, and fruits. The term "locus" is intended to include soil, seeds, and seedlings, as well as established vegetation. The term "metabolism" as used herein means the conversion or breakdown of a substance from one form to another by a living organism, in particular in a plant (in planta).

The term "salt" as used herein means a compound of formula (I) which has a negative charge, for example, on an oxygen atom of a hydroxyl or of a carboxyl group, or a compound of formula (I) which has a positive charge, for example, on a nitrogen atom in a nitrogen-containing heteroaryl group, for example if a such a nitrogen is quarternised by alkylation. The counter ion is necessarily of the opposite charge. Where the counter ion needs to be a cation the counter ion could be, for example, an alkali metal such as sodium or potassium, or an alkaline earth metal such as magnesium and calcium, or a quaternary ammonium base such as ammonium and tetramethylammonium. Where the counter ion needs to be a cation the counter ion could be, for example, hydroxide, or a halide such as chloride or bromide.

The compounds of formula (I) according to the invention also include hydrates which may be formed, for example, during salt formation.

Preferred values of $A^1$, $A^2$, $A^3$, $A^4$, $R^1$, $R^3$, $R^4$, $R^5$, $R^6$, $R^7$, $R^8$, $R^9$, $R^{10}$, $R^{11}$, $R^{12}$, $R^{13}$ and $R^{14}$ are, in any combination, as set out below.

Preferably up to three of $A^1$, $A^2$, $A^3$ and $A^4$ are N.

More preferably up to two of $A^1$, $A^2$, $A^3$ and $A^4$ are N.

Most preferably one of $A^1$, $A^2$, $A^3$ and $A^4$ is N.

Preferably each $R^1$ is hydrogen, $C_1$-$C_4$alkyl, $C_1$-$C_4$haloalkyl, halo, cyano, hydroxy or $C_1$-$C_4$alkoxy.

More preferably each $R^1$ is hydrogen, $C_1$-$C_4$alkyl, halo, cyano or hydroxy.

Even more preferably each $R^1$ is hydrogen, methyl, chloro or bromo.

Yet even more preferably each $R^1$ is hydrogen or chloro.

Most preferably each $R^1$ is hydrogen.

Preferably $R^3$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl. Examples of such preferred groups for $R^3$ are hydrogen, methyl, ethyl, n-propyl, iso-propyl, n-butyl, 2-methyl-propyl, 2-fluoro-ethyl, 2,2-difluoro-ethyl, 2,2,2-trifluoro-ethyl, allyl, but-3-en-1-yl or propargyl.

More preferably $R^3$ is hydrogen, $C_1$-$C_2$alkyl, $C_1$-$C_2$haloalkyl, $C_2$-$C_3$alkenyl or $C_2$-$C_3$alkynyl. Examples of such more preferred groups for $R^3$ are hydrogen, methyl, ethyl, 2,2-difluoro-ethyl, 2,2,2-trifluoro-ethyl, allyl or propargyl.

Most preferably $R^3$ is hydrogen, $C_1$-$C_2$alkyl, $C_1$-$C_2$haloalkyl or $C_2$-$C_3$alkynyl. Examples of such most preferred groups for $R^3$ are hydrogen, methyl, ethyl, 2,2-difluoro-ethyl or propargyl.

In one preferred embodiment $R^3$ is 2,2-difluoro-ethyl.

Preferably $R^4$ is aryl or aryl substituted by one to four $R^8$, which may be the same or different, or heteroaryl or heteroaryl substituted by one to three $R^8$, which may be the same or different.

More preferably $R^4$ is aryl substituted by two to three $R^8$, which may be the same or different, or $R^4$ is a monocyclic heteroaryl, containing up to two heteroatoms, substituted by one to three $R^8$, which may be the same of different, or $R^4$ is a bicyclic heteroaryl, containing up to three heteroatoms, substituted by one to three $R^8$, which may be the same of different.

Most preferably $R^4$ is phenyl substituted by two to three $R^8$, or $R^4$ is pyridyl, pyrimidinyl, thiophenyl, isoxazolyl, oxadiazolyl, or thiazolyl, substituted by one to three $R^8$, which may be the same or different, or $R^4$ is quinolinyl or isoquinolinyl, substituted by one to three $R^8$, which may be the same or different.

In one preferred embodiment $R^4$ is 2,5-bis-(trifluoromethyl)-phenyl.

In one preferred embodiment $R^4$ is 3-bromo-2-chloro-6-fluoro-phenyl.

In one preferred embodiment $R^4$ is 2-chloro-3,6-difluoro-phenyl.

In one preferred embodiment $R^4$ is 2-chloro-5-fluoro-phenyl.

In one preferred embodiment $R^4$ is 2-chloro-5-trifluoromethyl-phenyl.

In one preferred embodiment $R^4$ is 2-chloro-6-trifluoromethyl-phenyl.

In one preferred embodiment $R^4$ is 2,3-dichloro-6-fluoro-phenyl.

In one preferred embodiment $R^4$ is 2,6-dichloro-phenyl.

In one preferred embodiment $R^4$ is 2,6-dichloro-4-trifluoromethoxy-phenyl.

In one preferred embodiment $R^4$ is 2,3,6-trichloro-phenyl.

In one preferred embodiment $R^4$ is 3,5-dichloro-pyrid-2-yl.

In one preferred embodiment $R^4$ is 3,5-dichloro-pyrid-4-yl.

In one preferred embodiment $R^4$ is 2,6-dichloro-pyrid-3-yl.

In one preferred embodiment $R^4$ is 2,4-dichloro-pyrid-3-yl.

In one preferred embodiment $R^4$ is 4,6-dichloro-pyrid-3-yl.

In one preferred embodiment $R^4$ is 2,5-dichloro-pyrid-4-yl.

In one preferred embodiment $R^4$ is 3-trifluoromethyl-isoxazol-5-yl.

In one preferred embodiment $R^4$ is 3-methyl-1,2,4-oxadiazol-5-yl.

In one preferred embodiment $R^4$ is 2-chloro-4-methyl-thiazol-5-yl.

Preferably $R^5$ is hydroxy, $R^9$-oxy-, $R^{10}$-carbonyloxy-, tri-$R^{11}$-silyloxy- or $R^{12}$-sulfonyloxy-, wherein
$R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;
$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different;
each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;
$R^{12}$ is $C_1$-$C_{10}$alkyl, $C_1$-$C_{10}$haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and
each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_1$-$C_4$haloalkylsulfinyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy.

More preferably $R^5$ is hydroxy, $R^9$-oxy- or $R^{10}$-carbonyloxy-.

Even more preferably $R^5$ is hydroxy, $C_1$-$C_4$alkoxy, $C_1$-$C_4$alkenyloxy, $C_1$-$C_4$alkynyloxy, aryl-$C_1$-$C_4$alkoxy or aryl-$C_1$-$C_4$alkoxy wherein the aryl moiety is substituted by one to three $R^{14}$, which may be the same or different, heteroaryl-$C_1$-$C_4$alkoxy or heteroaryl-$C_1$-$C_4$alkoxy wherein the heteroaryl moiety is substituted by one to three $R^{14}$, which may be the same or different, $C_1$-$C_4$alkylcarbonyloxy-, $C_3$-$C_6$cyclo-alkylcarbonyloxy-, $C_3$-$C_{10}$cycloalkyl-$C_1$-$C_{10}$alkylcarbonyloxy-, $C_1$-$C_4$haloalkylcarbonyl-oxy-, $C_2$-$C_4$alkenylcarbonyloxy-, $C_2$-$C_4$alkynylcarbonyloxy-, $C_1$-$C_4$alkoxy-$C_1$-$C_4$alkylcarbonyloxy-, $C_1$-$C_4$alkylthio-$C_1$-$C_4$alkylcarbonyloxy-, $C_1$-$C_4$alkoxycarbonyloxy-, $C_2$-$C_4$alkenyloxycarbonyloxy-, $C_2$-$C_4$alkynyloxycarbonyloxy-, $C_1$-$C_4$alkylthiocarbonyloxy-, N—$C_1$-$C_4$alkyl-aminocarbonyloxy-, N,N-di-($C_1$-$C_4$alkyl)-aminocarbonyloxy-, arylcarbonyloxy- or arylcarbonyloxy-substituted by one to three $R^{14}$, which may be the same or different, heteroarylcarbonyloxy- or heteroarylcarbonyloxy-substituted by one to three $R^{14}$, which may be the same or different, aryl-$C_1$-$C_4$alkylcarbonyloxy- or aryl-$C_1$-$C_4$alkylcarbonyloxy-wherein the aryl moiety is substituted by one to three $R^{14}$, which may be the same or different, heteroaryl-$C_1$-$C_4$alkylcarbonyloxy- or heteroaryl-$C_1$-$C_4$alkylcarbonyloxy-wherein the heteroaryl moiety is substituted by one to three $R^{14}$, which may be the same or different, aryloxycarbonyloxy- or aryloxycarbonyloxy-substituted by one to three $R^{14}$, which may be the same or different, heteroaryloxycarbonyloxy- or heteroaryloxycarbonyloxy-substituted by one to three $R^{14}$, which may be the same or different, arylthiocarbonyloxy- or arylthiocarbonyloxy-substituted by one to three $R^{14}$, which may be the same or different, or heteroarylthiocarbonyloxy- or heteroarylthiocarbonyloxy-substituted by one to three $R^{14}$, which may be the same or different. Examples of preferred groups for $R^5$ are hydroxy, methoxy, ethoxy, allyloxy, propargyloxy, benzyloxy, methylcarbonyloxy-, ethylcarbonyloxy-, iso-propylcarbonyl-oxy-, n-propylcarbonyloxy-, but-2-ylcarbonyloxy-, 2-methyl-propylcarbonyloxy-, tert-butylcarbonyloxy-, cyclopropylcarbonyloxy-, cyclopentyl-methylcarbonyloxy-, chloromethylcarbonyloxy-, trifluoromethylcarbonyloxy-, allylcarbonyloxy-, (E)-prop-1-en-1-ylcarbonyloxy-, 2-methyl-prop-1-en-1-ylcarbonyloxy-, methoxymethylcarbonyloxy-, ethoxycarbonyloxy-, tert-butoxycarbonyloxy-, but-2-yn-1-yloxycarbonyloxy-, ethylthiocarbonyloxy-, N,N-diethylaminocarbonyloxy-, phenylcarbonyloxy-, 3-methoxy-phenylcarbonyloxy-, 4-nitro-phenylcarbonyloxy-, benzylcarbonyloxy-, furan-2-ylcarbonyloxy-, 2,5-dimethyl-furan-3-ylcarbonyloxy-, thiophen-2-ylcarbonyloxy-, 3,5-dimethyl-isoxazol-4-ylcarbonyloxy-, and 1-phenyl-prop-1-ylcarbonyloxy-.

Yet even more preferably $R^5$ is hydroxy, $C_1$-$C_4$alkylcarbonyloxy-, $C_3$-$C_6$cyclo-alkylcarbonyloxy-, $C_2$-$C_4$alkenylcarbonyloxy-, $C_2$-$C_4$alkynylcarbonyloxy-, $C_1$-$C_4$alkoxycarbonyloxy-, $C_2$-$C_4$alkenyloxycarbonyloxy-, $C_2$-$C_4$alkynyloxycarbonyloxy- or $C_1$-$C_4$alkylthiocarbonyloxy-. Examples of more preferred groups for $R^5$ are hydroxy, methylcarbonyloxy-, ethylcarbonyloxy-, iso-propylcarbonyloxy-, n-propylcarbonyloxy-, but-2-ylcarbonyloxy-, 2-methyl-propylcarbonyloxy-, tert-butylcarbonyloxy-, cyclopropylcarbonyloxy-, allylcarbonyloxy-, (E)-prop-1-en-1-ylcarbonyloxy-, 2-methyl-prop-1-en-1-ylcarbonyloxy-, ethoxycarbonyloxy-, tert-butoxycarbonyloxy-, but-2-yn-1-yloxycarbonyloxy-, and ethylthiocarbonyloxy-.

Most preferably $R^5$ is hydroxy, $C_1$-$C_4$alkylcarbonyloxy-, $C_1$-$C_4$alkoxycarbonyloxy- or $C_1$-$C_4$alkylthiocarbonyloxy-. Examples of most preferred groups for $R^5$ are hydroxy, methylcarbonyloxy-, ethylcarbonyloxy-, iso-propylcarbonyloxy-, n-propyl-carbonyloxy-, but-2-ylcarbonyloxy-, 2-methyl-propylcarbonyloxy-, tert-butylcarbonyloxy-, ethoxycarbonyloxy-, and ethylthiocarbonyloxy-.

In one preferred embodiment $R^5$ is hydroxy.

In one preferred embodiment $R^5$ is $R^9$-oxy-, wherein $R^9$ is $C_1$-$C_{10}$alkyl, $C_2$-$C_{10}$alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy. Such $R^5$ groups may be metabolised, preferably in planta, to give the corresponding compound wherein $R^5$ is hydroxy.

In one preferred embodiment $R^5$ is $R^{10}$-carbonyloxy-, wherein $R^{10}$ is $C_1$-$C_{10}$alkyl, $C_3$-$C_{10}$cycloalkyl, $C_1$-$C_{10}$haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy-substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio-substituted by one to three $R^{14}$, which may be the same or different; and each $R^{14}$ is independently halo, cyano, nitro, $C_1$-$C_{10}$alkyl, $C_1$-$C_4$haloalkyl, $C_1$-$C_{10}$alkoxy, $C_{10}$alkoxycarbonyl-, $C_1$-$C_4$haloalkoxy, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy. Such $R^5$ groups may be metabolised, preferably in planta, to give the corresponding compound wherein $R^5$ is hydroxy.

In one preferred embodiment $R^5$ is iso-propylcarbonyloxy- or tert-butylcarbonyloxy-.

Preferably each $R^6$ is independently halo, $C_1$-$C_4$alkyl, $C_1$-$C_4$haloalkyl, $C_1$-$C_4$alkoxy or $C_1$-$C_4$haloalkoxy. Examples of such preferred groups for $R^6$ are chloro, fluoro, methyl, ethyl, trifluoromethyl, methoxy or trifluoromethoxy.

Preferably each $R^7$ is independently halo, $C_1$-$C_4$alkyl, $C_1$-$C_4$haloalkyl, $C_1$-$C_4$alkoxy or $C_1$-$C_4$haloalkoxy. Examples of such preferred groups for $R^7$ are chloro, fluoro, methyl, ethyl, trifluoromethyl, methoxy and trifluoromethoxy.

Most preferably each $R^7$ is independently halo, $C_1$-$C_4$alkyl, $C_1$-$C_4$haloalkyl or $C_1$-$C_4$alkoxy. Examples of such preferred groups for $R^7$ are chloro, fluoro, methyl, ethyl, trifluoromethyl and methoxy.

Preferably each $R^8$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl- or $C_1$-$C_4$haloalkylsulfonyl-.

More preferably each $R^8$ is independently halo, cyano, nitro, $C_1$-$C_{10}$alkyl, $C_4$haloalkyl, $C_1$-$C_{10}$alkoxy, $C_1$-$C_4$haloalkoxy, $C_1$-$C_{10}$alkylthio or $C_1$-$C_4$haloalkylthio. Examples of such more preferred groups for $R^8$ are iodo, bromo, chloro, fluoro, cyano, nitro, methyl, ethyl, trifluoromethyl, methoxy, trifluoromethoxy or trifluoromethylthio.

Most preferably each $R^8$ is independently halo, $C_1$-$C_{10}$alkyl, $C_1$-$C_4$haloalkyl, $C_1$-$C_{10}$alkoxy or $C_1$-$C_4$haloalkoxy. Examples of such most preferred groups for $R^8$ are bromo, chloro, fluoro, methyl, ethyl, trifluoromethyl, methoxy or trifluoromethoxy.

Preferably $R^9$ is $C_2$-$C_{10}$alkenyl, $C_2$-$C_{10}$alkynyl, aryl-$C_1$-$C_4$alkyl- or aryl-$C_1$-$C_4$alkyl- wherein the aryl moiety is substituted by one to three $R^{13}$, which may be the same or different.

More preferably $R^9$ is $C_3$-$C_4$alkenyl, or $C_3$-$C_4$alkynyl, benzyl or benzyl wherein the phenyl moiety is substituted by one to three $R^{13}$, which may be the same or different.

Even more preferably $R^9$ is allyl, propargyl or benzyl.
Most preferably $R^9$ is allyl.

Preferably $R^{10}$ is $C_1$-$C_4$alkyl, $C_3$-$C_6$cycloalkyl, $C_3$-$C_{10}$cycloalkyl-$C_1$-$C_{10}$alkyl, $C_1$-$C_4$haloalkyl, $C_2$-$C_4$alkenyl, $C_2$-$C_4$alkynyl, $C_1$-$C_4$alkoxy-$C_1$-$C_4$alkyl, $C_1$-$C_4$alkylthio-$C_1$-$C_4$alkyl, $C_1$-$C_4$alkoxy, $C_2$-$C_4$alkenyloxy, $C_2$-$C_4$alkynyloxy, $C_1$-$C_4$alkylthio, N—$C_1$-$C_4$alkyl-amino, N,N-di-($C_1$-$C_4$alkyl)-amino, aryl or aryl substituted by one to three $R^{14}$, which may be the same or different, heteroaryl or heteroaryl substituted by one to three $R^{14}$, which may be the same or different, aryl-$C_1$-$C_4$alkyl or aryl-$C_1$-$C_4$alkyl wherein the aryl moiety is substituted by one to three $R^{14}$, which may be the same or different, heteroaryl-$C_1$-$C_4$alkyl or heteroaryl-$C_1$-$C_4$alkyl wherein the heteroaryl moiety is substituted by one to three $R^{14}$, which may be the same or different, aryloxy or aryloxy substituted by one to three $R^{14}$, which may be the same or different, heteroaryloxy or heteroaryloxy substituted by one to three $R^{14}$, which may be the same or different, arylthio or arylthio substituted by one to three $R^{14}$, which may be the same or different, or heteroarylthio or heteroarylthio substituted by one to three $R^{14}$, which may be the same or different.

Most preferably $R^{10}$ is iso-propyl or tert-butyl.
Preferably each $R^{11}$ is independently $C_1$-$C_4$alkyl.
Preferably $R^{12}$ is $C_1$-$C_4$alkyl or $C_1$-$C_4$haloalkyl.
Preferably each $R^{13}$ is independently halo, nitro, $C_1$-$C_4$alkyl, $C_1$-$C_4$haloalkyl or $C_1$-$C_4$alkoxy. Examples of such preferred groups are chloro, fluoro, nitro, methyl, ethyl, trifluoromethyl and methoxy.

Preferably each $R^{14}$ is independently halo, nitro, $C_1$-$C_4$alkyl, $C_1$-$C_4$haloalkyl, $C_1$-$C_4$alkoxy or $C_1$-$C_4$haloalkoxy. Examples of such preferred groups are chloro, fluoro, nitro, methyl, ethyl, trifluoromethyl, methoxy and trifluoromethoxy.

In one embodiment the invention provides a method of controlling plants which comprises applying to the plants or to the locus thereof a herbicidally effective amount of a compound of formula (Ix)

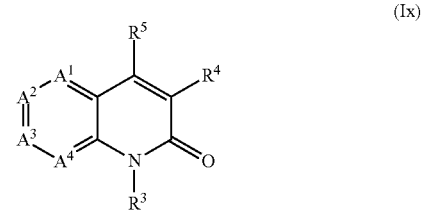

(Ix)

wherein $A^1$, $A^2$, $A^3$, $A^4$, $R^4$ and $R^5$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof. The preferences for $A^1$, $A^2$, $A^3$, $A^4$, $R^4$, $R^5$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

In another embodiment the invention provides a method of controlling plants which comprises applying to the plants or to the locus thereof a herbicidally effective amount of a compound of formula (Ic)

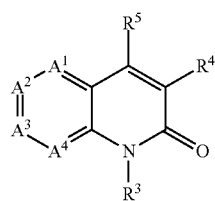

(Ic)

wherein $A^1$, $A^2$, $A^3$, $A^4$ and are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; and $R^5$ is a group which can be metabolised to a hydroxy group; or a salt or N-oxide thereof. The preferences for $A^1$, $A^2$, $A^3$, $A^4$, $R^4$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen. The preferences for $R^5$ are the same as the preferences set out for the corresponding substituents of a compound of formula (I) except that $R^5$ cannot be hydroxy.

In another embodiment the invention provides a method of controlling plants which comprises applying to the plants or to the locus thereof a herbicidally effective amount of a compound of formula (Id)

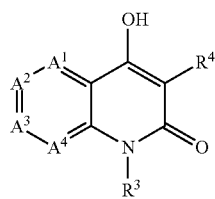

(Id)

wherein $A^1$, $A^2$, $A^3$, $A^4$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxylcarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof. The preferences for $A^1$, $A^2$, $A^3$, $A^4$, $R^4$, $R^6$, $R^7$, $R^8$ and $R^{13}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

Certain compounds of formula (I) are novel and as such form a further aspect of the invention. One group of novel compounds are compounds of formula (Ib)

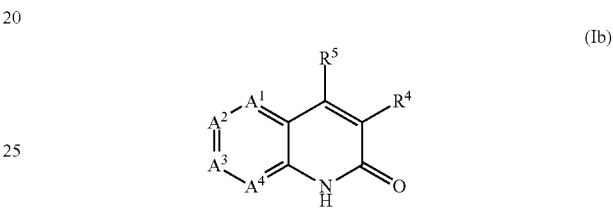

(Ib)

wherein $A^1$, $A^2$, $A^3$, $A^4$ and $R^4$ are as defined for compounds of formula (I) and $R^5$ is a group which can be metabolised to a hydroxy group; or a salt or N-oxide thereof. The preferences for $A^1$, $A^2$, $A^3$, $A^4$, $R^1$, $R^4$, $R^6$, $R^8$, $R^9$, $R^{10}$, $R^{11}$, $R^{12}$, $R^{13}$ and $R^{14}$ are the same as the preferences set out for the corresponding substituents of compounds of the formula (I). The preferences for $R^5$ are the same as the preferences set out for the corresponding substituents of compounds of formula (I) except that $R^5$ cannot be hydroxy.

Another group of novel compounds are compounds of formula (Ic)

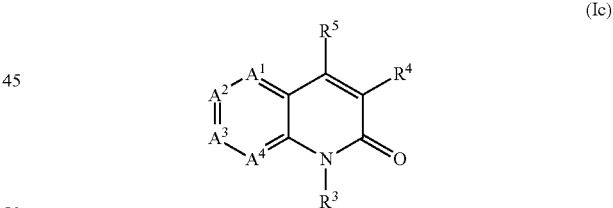

(Ic)

wherein $A^1$, $A^2$, $A^3$, $A^4$ and $R^4$ are as defined for a compound of formula (I) and $R^3$ is $C_1$-$C_{10}$alkyl, $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N, N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; and $R^5$ is a group which can be metabolised to a hydroxy group; or a salt or N-oxide thereof; provided that the compound is not 2-[4-(acetyloxy)-1,2-dihydro-2-oxo-1-phenyl-1,8-naphthyridin-3-yl]-1-methyl-pyridinium (CAS RN 115892-38-1). The preferences for $A^1$, $A^2$, $A^3$, $A^4$, $R^1$, $R^4$, $R^6$, $R^7$, $R^8$, $R^9$, $R^{10}$, $R^{11}$, $R^{12}$, $R^{13}$ and $R^{14}$ are the same as the preferences set out for the corresponding substituents of a compound of formula (I). The preferences for $R^3$ are the same as the preferences set out for the corresponding substituents of a compound of formula (I) except that $R^3$ cannot be hydrogen. The preferences for $R^5$ are the same as the preferences set out for the corresponding substituents of a compound of formula (I) except that $R^5$ cannot be hydroxy.

A further group of novel compounds are compounds of formula (Id)

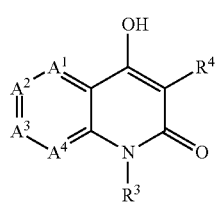

(Id)

wherein $A^1$, $A^2$, $A^3$, $A^4$ and $R^4$ are as defined for a compound of formula (I) and $R^3$ is $C_2$-$C_{10}$alkenyl, $C_2$-$C_{10}$alkynyl, $C_3$-$C_{10}$cycloalkyl, $C_3$-$C_{10}$cycloalkyl-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different; or a salt or N-oxide thereof; provided that the compound is not 4-hydroxy-1-methyl-3-(2,4,6-trimethylphenyl)-1,8-naphthyridin-2(1H)-one (CAS RN 380634-13-9), 6-chloro-4-hydroxy-1-methyl-3-(thien-3-yl)-1,8-naphthyridin-2(1H)-one (CAS RN 174347-23-0), 6-chloro-4-hydroxy-1-methyl-3-(thien-3-yl)-1,8-naphthyridin-2(1H)-one sodium salt (CAS RN 174347-24-1), or 6-chloro-1-ethyl-4-hydroxy-3-(thien-3-yl)-1,8-naphthyridin-2(1H)-one. The preferences for $A^1$, $A^2$, $A^3$, $A^4$, $R^1$, $R^4$, $R^6$, $R^7$, $R^8$ and $R^{13}$ are the same as the preferences set out for the corresponding substituents of a compound of formula (I). The preferences for $R^3$ are the same as the preferences set out for the corresponding substituents of a compound of formula (I) except that $R^3$ cannot be hydrogen.

The compounds in Tables 1 to 41 below illustrate the compounds of the invention.

TABLE 1

Table 1 provides 70 compounds of formula (I'), where $R^4$ is 2,5-bis-(trifluoromethyl)-phenyl, and $R^3$ and $R^5$ have the values listed in Table 1.

(I')

| Compound number | $R^3$ | $R^5$ |
|---|---|---|
| 1.001 | H | —OH |
| 1.002 | H | —OCOCH$_3$ |
| 1.003 | H | —OCOCH$_2$CH$_3$ |
| 1.004 | H | —OCOCH(CH$_3$)$_2$ |
| 1.005 | H | —OCO(CH$_2$)$_2$CH$_3$ |
| 1.006 | H | —OCOCH(CH$_3$)CH$_2$CH$_3$ |
| 1.007 | H | —OCOCH$_2$CH(CH$_3$)$_2$ |
| 1.008 | H | —OCOC(CH$_3$)$_3$ |
| 1.009 | H | —O(CO)OCH$_2$CH$_3$ |
| 1.010 | H | —O(CO)SCH$_2$CH$_3$ |
| 1.011 | —CH$_3$ | —OH |
| 1.012 | —CH$_3$ | —OCOCH$_3$ |
| 1.013 | —CH$_3$ | —OCOCH$_2$CH$_3$ |
| 1.014 | —CH$_3$ | —OCOCH(CH$_3$)$_2$ |
| 1.015 | —CH$_3$ | —OCO(CH$_2$)$_2$CH$_3$ |
| 1.016 | —CH$_3$ | —OCOCH(CH$_3$)CH$_2$CH$_3$ |
| 1.017 | —CH$_3$ | —OCOCH$_2$CH(CH$_3$)$_2$ |
| 1.018 | —CH$_3$ | —OCOC(CH$_3$)$_3$ |
| 1.019 | —CH$_3$ | —O(CO)OCH$_2$CH$_3$ |
| 1.020 | —CH$_3$ | —O(CO)SCH$_2$CH$_3$ |
| 1.021 | —CH$_2$CH$_3$ | —OH |
| 1.022 | —CH$_2$CH$_3$ | —OCOCH$_3$ |
| 1.023 | —CH$_2$CH$_3$ | —OCOCH$_2$CH$_3$ |
| 1.024 | —CH$_2$CH$_3$ | —OCOCH(CH$_3$)$_2$ |
| 1.025 | —CH$_2$CH$_3$ | —OCO(CH$_2$)$_2$CH$_3$ |
| 1.026 | —CH$_2$CH$_3$ | —OCOCH(CH$_3$)CH$_2$CH$_3$ |
| 1.027 | —CH$_2$CH$_3$ | —OCOCH$_2$CH(CH$_3$)$_2$ |
| 1.028 | —CH$_2$CH$_3$ | —OCOC(CH$_3$)$_3$ |
| 1.029 | —CH$_2$CH$_3$ | —O(CO)OCH$_2$CH$_3$ |
| 1.030 | —CH$_2$CH$_3$ | —O(CO)SCH$_2$CH$_3$ |
| 1.031 | —CH$_2$CHF$_2$ | —OH |
| 1.032 | —CH$_2$CHF$_2$ | —OCOCH$_3$ |

TABLE 1-continued

Table 1 provides 70 compounds of formula (I'), where $R^4$ is 2,5-bis-(trifluoromethyl)-phenyl, and $R^3$ and $R^5$ have the values listed in Table 1.

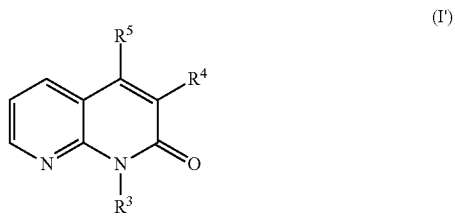

(I')

| Compound number | $R^3$ | $R^5$ |
|---|---|---|
| 1.033 | —CH$_2$CHF$_2$ | —OCOCH$_2$CH$_3$ |
| 1.034 | —CH$_2$CHF$_2$ | —OCOCH(CH$_3$)$_2$ |
| 1.035 | —CH$_2$CHF$_2$ | —OCO(CH$_2$)$_2$CH$_3$ |
| 1.036 | —CH$_2$CHF$_2$ | —OCOCH(CH$_3$)CH$_2$CH$_3$ |
| 1.037 | —CH$_2$CHF$_2$ | —OCOCH$_2$CH(CH$_3$)$_2$ |
| 1.038 | —CH$_2$CHF$_2$ | —OCOC(CH$_3$)$_3$ |
| 1.039 | —CH$_2$CHF$_2$ | —O(CO)OCH$_2$CH$_3$ |
| 1.040 | —CH$_2$CHF$_2$ | —O(CO)SCH$_2$CH$_3$ |
| 1.041 | —CH$_2$CF$_3$ | —OH |
| 1.042 | —CH$_2$CF$_3$ | —OCOCH$_3$ |
| 1.043 | —CH$_2$CF$_3$ | —OCOCH$_2$CH$_3$ |
| 1.044 | —CH$_2$CF$_3$ | —OCOCH(CH$_3$)$_2$ |
| 1.045 | —CH$_2$CF$_3$ | —OCO(CH$_2$)$_2$CH$_3$ |
| 1.046 | —CH$_2$CF$_3$ | —OCOCH(CH$_3$)CH$_2$CH$_3$ |
| 1.047 | —CH$_2$CF$_3$ | —OCOCH$_2$CH(CH$_3$)$_2$ |
| 1.048 | —CH$_2$CF$_3$ | —OCOC(CH$_3$)$_3$ |
| 1.049 | —CH$_2$CF$_3$ | —O(CO)OCH$_2$CH$_3$ |
| 1.050 | —CH$_2$CF$_3$ | —O(CO)SCH$_2$CH$_3$ |
| 1.051 | —CH$_2$CH=CH$_2$ | —OH |
| 1.052 | —CH$_2$CH=CH$_2$ | —OCOCH$_3$ |
| 1.053 | —CH$_2$CH=CH$_2$ | —OCOCH$_2$CH$_3$ |
| 1.054 | —CH$_2$CH=CH$_2$ | —OCOCH(CH$_3$)$_2$ |
| 1.055 | —CH$_2$CH=CH$_2$ | —OCO(CH$_2$)$_2$CH$_3$ |
| 1.056 | —CH$_2$CH=CH$_2$ | —OCOCH(CH$_3$)CH$_2$CH$_3$ |
| 1.057 | —CH$_2$CH=CH$_2$ | —OCOCH$_2$CH(CH$_3$)$_2$ |
| 1.058 | —CH$_2$CH=CH$_2$ | —OCOC(CH$_3$)$_3$ |
| 1.059 | —CH$_2$CH=CH$_2$ | —O(CO)OCH$_2$CH$_3$ |
| 1.060 | —CH$_2$CH=CH$_2$ | —O(CO)SCH$_2$CH$_3$ |
| 1.061 | —CH$_2$C≡CH | —OH |
| 1.062 | —CH$_2$C≡CH | —OCOCH$_3$ |
| 1.063 | —CH$_2$C≡CH | —OCOCH$_2$CH$_3$ |
| 1.064 | —CH$_2$C≡CH | —OCOCH(CH$_3$)$_2$ |
| 1.065 | —CH$_2$C≡CH | —OCO(CH$_2$)$_2$CH$_3$ |
| 1.066 | —CH$_2$C≡CH | —OCOCH(CH$_3$)CH$_2$CH$_3$ |
| 1.067 | —CH$_2$C≡CH | —OCOCH$_2$CH(CH$_3$)$_2$ |
| 1.068 | —CH$_2$C≡CH | —OCOC(CH$_3$)$_3$ |
| 1.069 | —CH$_2$C≡CH | —O(CO)OCH$_2$CH$_3$ |
| 1.070 | —CH$_2$C≡CH | —O(CO)SCH$_2$CH$_3$ |

Table 2:

Table 2 provides 70 compounds of formula (I'), where $R^4$ is 3-bromo-2-chloro-6-fluoro-phenyl, and $R^3$ and $R^5$ have the values listed in Table 1.

Table 3:

Table 3 provides 70 compounds of formula (I'), where $R^4$ is 2-chloro-3,6-difluoro-phenyl, and $R^3$ and $R^5$ have the values listed in Table 1.

Table 4:

Table 4 provides 70 compounds of formula (I'), where $R^4$ is 2-chloro-4-fluoro-phenyl, and $R^3$ and $R^5$ have the values listed in Table 1.

Table 5:

Table 5 provides 70 compounds of formula (I'), where $R^4$ is 2-chloro-5-fluoro-phenyl, and $R^3$ and $R^5$ have the values listed in Table 1.

Table 6:

Table 6 provides 70 compounds of formula (I'), where $R^4$ is 2-chloro-phenyl, and $R^3$ and $R^5$ have the values listed in Table 1.

Table 7:

Table 7 provides 70 compounds of formula (I'), where $R^4$ is 2-chloro-3-trifluoromethyl-phenyl, and $R^3$ and $R^5$ have the values listed in Table 1.

Table 8:

Table 8 provides 70 compounds of formula (I'), where $R^4$ is 2-chloro-5-trifluoromethyl-phenyl, and $R^3$ and $R^5$ have the values listed in Table 1.

Table 9:

Table 9 provides 70 compounds of formula (I'), where $R^4$ is 2-chloro-6-trifluoromethyl-phenyl, and $R^3$ and $R^5$ have the values listed in Table 1.

Table 10:
Table 10 provides 70 compounds of formula (I'), where $R^4$ is 2,3-dichloro-6-fluoro-phenyl, and $R^3$ and $R^5$ have the values listed in Table 1.
Table 11:
Table 11 provides 70 compounds of formula (I'), where $R^4$ is 2,4-dichloro-5-fluoro-phenyl, and $R^3$ and $R^5$ have the values listed in Table 1.
Table 12:
Table 12 provides 70 compounds of formula (I'), where $R^4$ is 3,5-dichloro-2-methoxy-phenyl, and $R^3$ and $R^5$ have the values listed in Table 1.
Table 13:
Table 13 provides 70 compounds of formula (I'), where $R^4$ is 2,3-dichloro-phenyl, and $R^3$ and $R^5$ have the values listed in Table 1.
Table 14:
Table 14 provides 70 compounds of formula (I'), where $R^4$ is 2,4-dichloro-phenyl, and $R^3$ and $R^5$ have the values listed in Table 1.
Table 15:
Table 15 provides 70 compounds of formula (I'), where $R^4$ is 2,5-dichloro-phenyl, and $R^3$ and $R^5$ have the values listed in Table 1.
Table 16:
Table 16 provides 70 compounds of formula (I'), where $R^4$ is 2,6-dichloro-phenyl, and $R^3$ and $R^5$ have the values listed in Table 1.
Table 17:
Table 17 provides 70 compounds of formula (I'), where $R^4$ is 2,6-dichloro-4-trifluoro-methoxy-phenyl, and $R^3$ and $R^5$ have the values listed in Table 1.
Table 18:
Table 18 provides 70 compounds of formula (I'), where $R^4$ is 2,6-dichloro-4-trifluoromethyl-phenyl, and $R^3$ and $R^5$ have the values listed in Table 1.
Table 19:
Table 19 provides 70 compounds of formula (I'), where $R^4$ is 2,6-diethyl-4-methyl-phenyl, and $R^3$ and $R^5$ have the values listed in Table 1.
Table 20:
Table 20 provides 70 compounds of formula (I'), where $R^4$ is 2,3-dimethoxy-phenyl, and $R^3$ and $R^5$ have the values listed in Table 1.
Table 21:
Table 21 provides 70 compounds of formula (I'), where $R^4$ is 2-methoxy-5-trifluoro-methoxy-phenyl, and $R^3$ and $R^5$ have the values listed in Table 1.
Table 22:
Table 22 provides 70 compounds of formula (I'), where $R^4$ is 2,3,6-trichloro-phenyl, and $R^3$ and $R^5$ have the values listed in Table 1.
Table 23:
Table 23 provides 70 compounds of formula (I'), where $R^4$ is 2-trifluoromethoxy-phenyl, and $R^3$ and $R^5$ have the values listed in Table 1.
Table 24:
Table 24 provides 70 compounds of formula (I'), where $R^4$ is 2-trifluoromethyl-phenyl, and $R^3$ and $R^5$ have the values listed in Table 1.
Table 25:
Table 25 provides 70 compounds of formula (I'), where $R^4$ is 2,4,6-trimethyl-phenyl, and $R^3$ and $R^5$ have the values listed in Table 1.
Table 26:
Table 26 provides 70 compounds of formula (I'), where $R^4$ is 3,5-dichloro-pyrid-2-yl, and $R^3$ and $R^5$ have the values listed in Table 1.
Table 27:
Table 27 provides 70 compounds of formula (I'), where $R^4$ is 3,5-dichloro-pyrid-4-yl, and $R^3$ and $R^5$ have the values listed in Table 1.
Table 28:
Table 28 provides 70 compounds of formula (I'), where $R^4$ is 2,6-dichloro-pyrid-3-yl, and $R^3$ and $R^5$ have the values listed in Table 1.
Table 29:
Table 29 provides 70 compounds of formula (0, where $R^4$ is 2,4-dichloro-pyrid-3-yl, and $R^3$ and $R^5$ have the values listed in Table 1.
Table 30:
Table 30 provides 70 compounds of formula (I'), where $R^4$ is 4,6-dichloro-pyrid-3-yl, and $R^3$ and $R^5$ have the values listed in Table 1.
Table 31:
Table 31 provides 70 compounds of formula (I'), where $R^4$ is 2,5-dichloro-pyrid-4-yl, and $R^3$ and $R^5$ have the values listed in Table 1.
Table 32:
Table 32 provides 70 compounds of formula (I'), where $R^4$ is 3,6-dichloro-pyrid-2-yl, and $R^3$ and $R^5$ have the values listed in Table 1.
Table 33:
Table 33 provides 70 compounds of formula (I'), where $R^4$ is 3-chloro-5-fluoro-pyrid-2-yl, and $R^3$ and $R^5$ have the values listed in Table 1.
Table 34:
Table 34 provides 70 compounds of formula (I'), where $R^4$ is 3-chloro-5-trifluoromethyl-pyrid-2-yl, and $R^3$ and $R^5$ have the values listed in Table 1.
Table 35:
Table 35 provides 70 compounds of formula (I'), where $R^4$ is 3,5,6-trichloro-pyrid-2-yl, and $R^3$ and $R^5$ have the values listed in Table 1.
Table 36:
Table 36 provides 70 compounds of formula (I'), where $R^4$ is 3,5-dichloro-pyrid-3-yl, and $R^3$ and $R^5$ have the values listed in Table 1.
Table 37:
Table 37 provides 70 compounds of formula (I'), where $R^4$ is 2,3-dichloro-pyrid-4-yl, and $R^3$ and $R^5$ have the values listed in Table 1.
Table 38:
Table 38 provides 70 compounds of formula (I'), where $R^4$ is 2-chloro-4-trifluoromethyl-pyrid-3-yl, and $R^3$ and $R^5$ have the values listed in Table 1.
Table 39:
Table 39 provides 70 compounds of formula (I'), where $R^4$ is 2-chloro-6-trifluoromethyl-pyrid-3-yl, and $R^3$ and $R^5$ have the values listed in Table 1.
Table 40:
Table 40 provides 70 compounds of formula (I), where $R^4$ is 3-chloro-5-trifluoromethyl-pyrid-4-yl, and $R^3$ and $R^5$ have the values listed in Table 1.
Table 41:
Table 41 provides 70 compounds of formula (I'), where $R^4$ is 2,3,5-trichloro-pyrid-4-yl, and $R^3$ and $R^5$ have the values listed in Table 1.

The compounds of the invention may be made by a variety of methods, for example by the methods described in Schemes 1 to 4.

1) Compounds of formula (3) as shown in Scheme 1 wherein $A^1$, $A^2$, $A^3$ and $A^4$ are as defined for a compound of formula (I) and $R^{16}$ is $C_1$-$C_6$alkyl can be made by reaction of an aminopyrazine acid of formula (2) wherein $A^1$, $A^2$, $A^3$, $A^4$ are as defined for a compound of formula (I) via methods known to the person skilled in the art. For example, the transformation of an aminopyrazine acid to its methyl ester can conveniently be carried out in a suitable solvent mixture, such as methanol and toluene, using (trimethylsilyl)diazomethane as reagent.

2) Compounds of formula (5) wherein $A^1$, $A^2$, $A^3$, $A^4$ and $R^4$ are as defined for a compound of formula (I) and $R^{16}$ is $C_1$-$C_6$alkyl can be made by reaction of an amino-pyrazine ester of formula (3) as defined in 1) wherein $A^1$, $A^2$, $A^3$ and $A^4$ are as defined for a compound of formula (I) and $R^{16}$ is $C_1$-$C_6$alkyl with an acid derivative of formula (4) wherein $R^4$ is as defined for a compound of formula (I) and X is halogen or hydroxy. For example, if (4) is an acid chloride (i.e. where X is chlorine) the reaction can conveniently be carried out optionally in the presence of a base, such as triethylamine or pyridine, in a suitable solvent, such as acetonitrile or dichloromethane, optionally using microwave heating. Alternatively, if (4) is a carboxylic acid (i.e. where X is hydroxy) the reaction can conveniently be carried out using an amide coupling method, for example by reaction with a coupling agent, such as bis(2-oxo-3-oxazolidinyl)phosphinic chloride or N-(3-dimethylaminopropyl)-N'-ethylcarbodiimide hydrochloride ("EDAC"), in the presence of a base, such as triethylamine, in a suitable solvent, such as dichloromethane, or other amide coupling methods which have been reviewed in Tetrahedron (2005), 61(46), 10827-10852.

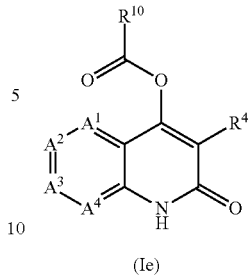

(Ie)

3) Compounds of formula (Ia) wherein $A^1$, $A^2$, $A^3$, $A^4$ and $R^4$ are as defined for a compound of formula (I) can be prepared by treating a compound of formula (5) as defined in 2) with a base in a suitable solvent, such as potassium carbonate in N,N-dimethylformamide or lithium hexamethyldisilazide in tetrahydrofuran, optionally using microwave heating.

4) Alternatively, where $R^4$ is heterocyclic and where (4) is a carboxylic ester (i.e. where X is $OR^{16}$ and $R^{16}$ is as defined in 1), the compounds of formula (Ia) as defined in 3) can also be prepared directly by reaction of a compound of formula (3) as defined in 1) with an carboxylic ester of formula (4) as defined here in the presence of a base, such as sodium ethoxide, in a suitable solvent, such as N,N-dimethylformamide, optionally using microwave heating.

5) Compounds of formula (Ie) wherein $A^1$, $A^2$, $A^3$, $A^4$, $R^4$ and $R^{10}$ are as defined for a compound of formula (I) can be prepared by reaction of a compound of formula (Ia) as defined in 3) with an acid chloride of formula $R^{10}COCl$ or an acid anhydride of formula $(R^{10}CO)_2O$ wherein $R^{10}$ is as defined for a compound of formula (I), optionally in the presence of a base, such as triethylamine or pyridine, optionally in a suitable solvent, such as dichloromethane, optionally using microwave heating.

Scheme 1

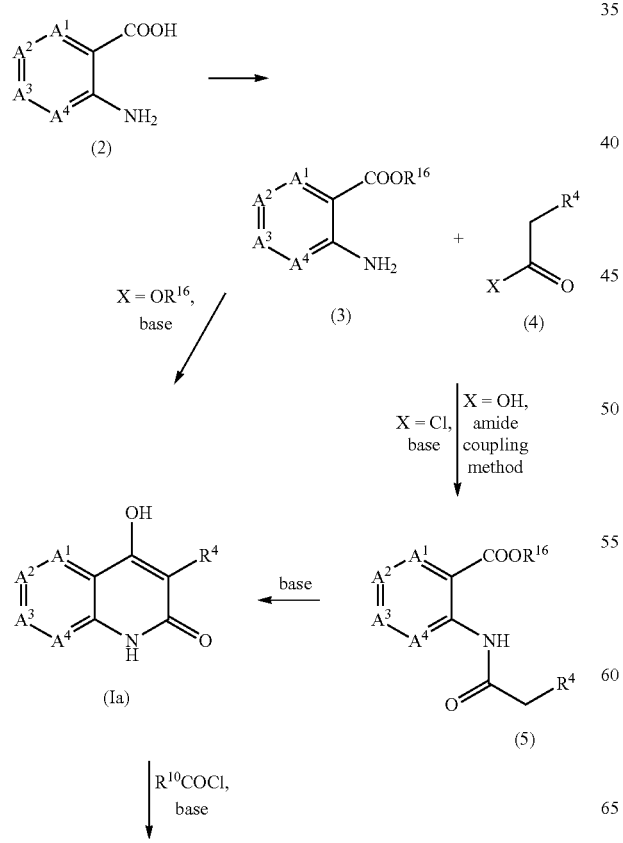

Scheme 2

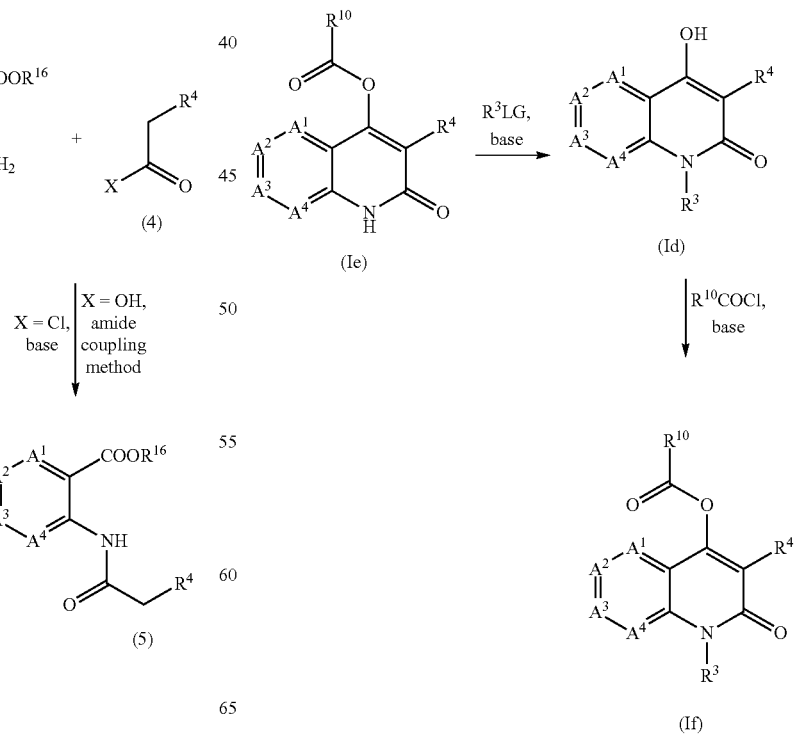

6) Compounds of formula (Id) wherein $A^1$, $A^2$, $A^3$, $A^4$, $R^3$ and $R^4$ are as defined for a compound of formula (I), with $R^3$ other than hydrogen, can be prepared by treating a compound of formula (Ie) as defined in 5) by reaction with a compound of formula $R^3LG$ wherein $R^3$ is as defined for a compound of formula (I) and LG is a leaving group such as a halide, for example bromide or iodide, or tosylate, mesylate or triflate, in the presence of a base, such as potassium carbonate, optionally in the presence of an activator/iodide, such as potassium iodide, in a suitable solvent, such as acetonitrile or N,N-dimethylformamide, optionally using microwave heating, as shown in Scheme 2.

7) Compounds of formula (If) wherein $A^1$, $A^2$, $A^3$, $A^4$, $R^3$, $R^4$ and $R^{10}$ are as defined for a compound of formula (I), with $R^3$ other than hydrogen, can be prepared by reaction of a compound of formula (Id) as defined in 6) with an acid chloride of formula $R^{10}COCl$ or an acid anhydride of formula $(R^{10}CO)_2O$ wherein $R^{10}$ is as defined for a compound of formula (I), optionally in the presence of a base, such as potassium tert-butoxide or pyridine, optionally in a suitable solvent, such as dichloromethane or tetrahydrofuran, optionally using microwave heating.

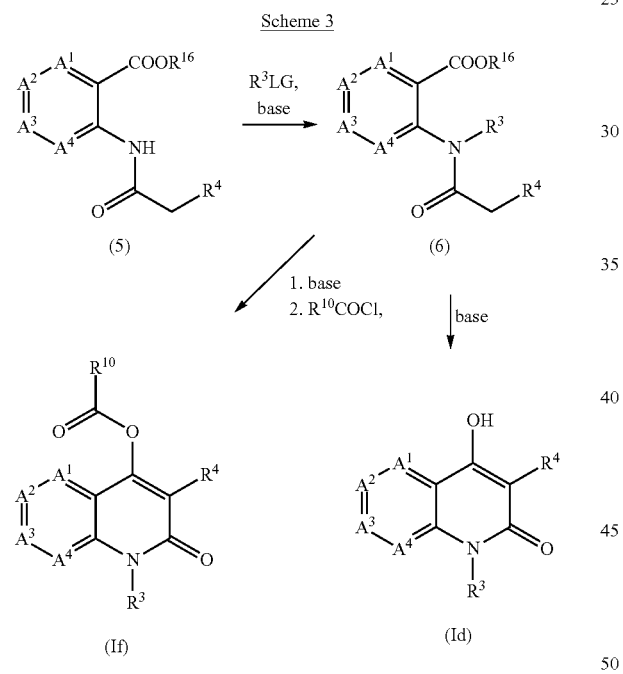

8) Compounds of formula (6) wherein $A^1$, $A^2$, $A^3$, $A^4$, $R^3$ and $R^4$ are as defined for a compound of formula (I), with $R^3$ other than hydrogen, and $R^{16}$ is as defined in 1) can be prepared by treating a compound of formula (5) as defined in 2) by reaction with a compound of formula $R^3LG$ as defined in 6), in the presence of a base, such as sodium hydride, in a suitable solvent, such as N,N-dimethylformamide, optionally using microwave heating, as shown in Scheme 3.

9) Compounds of formula (Id) as defined in 6), can be prepared by treating a compound of formula (6) as defined in 8) with a base, such as potassium tert-butoxide or lithium hexamethyldisilazide, in a suitable solvent, such as N,N-dimethylformamide or tetrahydrofuran, optionally using microwave heating.

10) Compounds of formula (If) as defined in 7), can be prepared in a one pot procedure by treating a compound of formula (6) as defined in 8) with a base, such as sodium hexamethyldisilazide, in a suitable solvent, such as tetrahydrofuran, followed by an acid chloride of formula $R^{10}COCl$ or an acid anhydride of formula $(R^{10}CO)_2O$ wherein $R^{10}$ is as defined for a compound of formula (I).

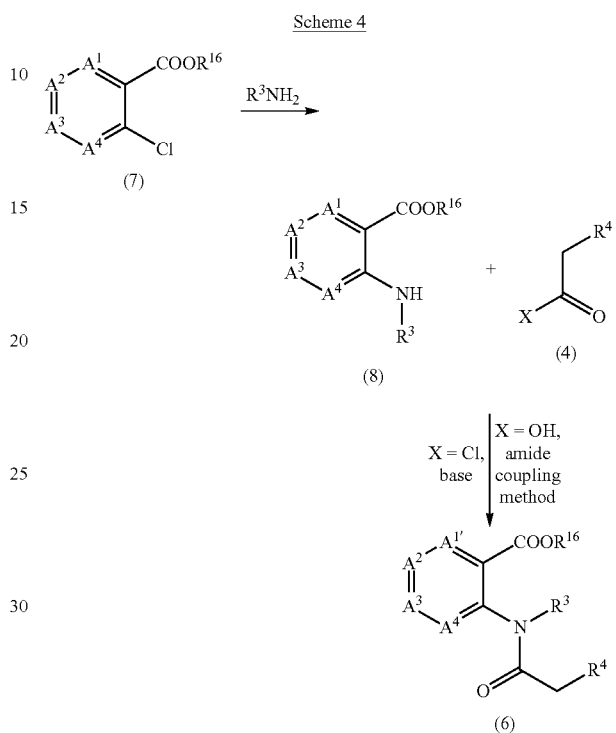

11) Compounds of formula (8) wherein $A^1$, $A^2$, $A^3$, $A^4$ and $R^3$ are as defined for a compound of formula (I), with $R^3$ other than hydrogen, and $R^{16}$ is as defined in 1) can be prepared from a compound of formula (7) wherein $A^1$, $A^2$, $A^3$ and $A^4$ are as defined for a compound of formula (I) and $R^{16}$ is as defined in 1) by reaction with an amine of formula $R^3NH_2$ wherein $R^3$ is as defined for a compound of formula (I) in the presence of a base, such as diisopropylethylamine, in a suitable solvent, such as ethanol, optionally using microwave heating, as shown in Scheme 4.

12) Compounds of formula (6) as defined in 8), can be prepared by treating a compound of formula (8) as defined in 11) with an acid derivative of formula (4) as defined in 2).

The compounds of formula (I) according to the invention can be used as herbicides in unmodified form, as obtained in the synthesis, but they are generally formulated into herbicidal compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO Specifications for Plant Protection Products, 5th Edition, 1999. Such formulations can either be used directly or they are diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof. The active ingredients can also be contained in very fine microcapsules consisting of a polymer. Microcapsules contain the active ingredients in a porous carrier. This enables the active ingredients to be released into the environment in controlled amounts (e.g. slow-release). Microcapsules usually have diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art in this connection. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octa-decanoic acid, octylamine acetate, oleic acid, oleylamine, o-xylene, phenol, polyethylene glycol (PEG400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like. Water is generally the carrier of choice for diluting the concentrates. Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances, as described, for example, in CFR 180.1001. (c) & (d).

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in "McCutcheon's Detergents and Emulsifiers Annual" MC Publishing Corp., Ridgewood N.J., 1981.

Further adjuvants that can usually be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and also liquid and solid fertilisers.

The compositions according to the invention can additionally include an additive comprising an oil of vegetable or animal origin, a mineral oil, alkyl esters of such oils or mixtures of such oils and oil derivatives. The amount of oil additive in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being of importance. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combination with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltriloxanes which are commercially available e.g. as Silwet L-77®, and also perfluorinated surfactants. The concentration of the surface-active substances in relation to the total additive is generally from 1 to 30% by weight. Examples of oil additives consisting of mixtures of oil or mineral oils or derivatives thereof with surfactants are Edenor ME SU®, Turbocharge® (Syngenta AG, CH) or ActipronC (BP Oil UK Limited, GB).

If desired, it is also possible for the mentioned surface-active substances to be used in the formulations on their own, that is to say without oil additives.

Furthermore, the addition of an organic solvent to the oil additive/surfactant mixture may contribute to an additional enhancement of action. Suitable solvents are, for example, Solvesso® (ESSO) or Aromatic Solvent® (Exxon Corporation). The concentration of such solvents can be from 10 to 80% by weight of the total weight. Oil additives that are present in admixture with solvents are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada).

In addition to the oil additives listed above, for the purpose of enhancing the action of the compositions according to the invention it is also possible for formulations of alkylpyrrolidones (e.g. Agrimax®) to be added to the spray mixture. Formulations of synthetic lattices, e.g. polyacrylamide, polyvinyl compounds or poly-1-p-menthene (e.g. Bond®, Courier® or Emerald®) may also be used. It is also possible for solutions that contain propionic acid, for example Eurogkem Pen-e-trate®, to be added to the spray mixture as action-enhancing agent.

The herbicidal compositions generally comprise from 0.1 to 99% by weight, especially from 0.1 to 95% by weight, compounds of formula (I) and from 1 to 99.9% by weight of a formulation adjuvant which preferably includes from 0 to 25% by weight of a surface-active substance. Whereas commercial products will preferably be formulated as concentrates, the end user will normally employ dilute formulations.

The rates of application of compounds of formula (I) may vary within wide limits and depend on the nature of the soil, the method of application (pre- or post-emergence; seed dressing; application to the seed furrow; no tillage application etc.), the crop plant, the grass or weed to be controlled, the prevailing climatic conditions, and other factors governed by the method of application, the time of application and the target crop. The compounds of formula (I) according to the invention are generally applied at a rate of from 10 to 2000 g/ha, especially from 50 to 1000 g/ha.

Preferred formulations have especially the following compositions (%=percent by weight):
Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

Formulation Examples for herbicides of formula (I) (%=% by weight)

| F1. Emulsifiable concentrates | a) | b) | c) | d) |
|---|---|---|---|---|
| active ingredient | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be obtained from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for use in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient | 0.1% | 5% | 15% |
| highly dispersed silicic acid | 0.9% | 2% | 2% |
| inorganic carrier (diameter 0.1-1 mm) e.g. $CaCO_3$ or $SiO_2$ | 99.0% | 93% | 83% |

The active ingredient is dissolved in methylene chloride and applied to the carrier by spraying, and the solvent is then evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silicic acid | 0.9% | 1% | 2% |
| inorganic carrier (diameter 0.1-1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

The invention relates to a method of controlling plants which comprises applying to the plants or to the locus thereof a herbicidally effective amount of a compound of formula (I).

The invention also relates to a method of inhibiting plant growth which comprises applying to the plants or to the locus thereof a herbicidally effective amount of a compound of formula (I).

The invention also relates to a method of selectively controlling grasses and weeds in crops of useful plants which comprises applying to the useful plants or locus thereof or to the area of cultivation a herbicidally effective amount of a compound of formula (I).

Crops of useful plants in which the composition according to the invention can be used include perennial crops, such as citrus fruit, grapevines, nuts, oil palms, olives, pome fruit, stone fruit and rubber, and annual arable crops, such as cereals, for example barley and wheat, cotton, oilseed rape, maize, rice, soy beans, sugar beet, sugar cane, sunflowers, ornamentals and vegetables, especially cereals, maize and soy beans.

The grasses and weeds to be controlled may be both monocotyledonous species, for example *Agrostis, Alopecurus, Avena, Bromus, Cyperus, Digitaria, Echinochloa, Lolium, Monochoria, Rottboellia, Sagittaria, Scirpus, Setaria, Sida* and *Sorghum*, and dicotyledonous species, for example *Abutilon, Amaranthus, Chenopodium, Chrysanthemum, Galium, Ipomoea, Nasturtium, Sinapis, Solanum, Stellaria, Veronica, Viola* and *Xanthium*.

Crops are to be understood as also including those crops which have been rendered tolerant to herbicides or classes of herbicides (e.g. auxins or ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesize such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

Areas under cultivation include land on which the crop plants are already growing and land intended for cultivation with those crop plants. The compounds of the invention can be applied before weeds emerge (pre-emergence application) or after weeds emerge (post-emergence application), and are particularly effective when applied post-emergence.

The compounds of formula (I) according to the invention can also be used in combination with one or more further herbicides. In particular, the following mixtures of the compound of formula (I) are important:

Mixtures of a compound of formula (I) with a synthetic auxin (e.g. compound of formula (I)+clopyralid (162), compound of formula (I)+2,4-D (211), compound of formula (I)+dicamba (228), compound of formula (I)+diphenamid (274), compound of formula (I)+MCPA (499), compound of formula (I)+quinclorac (712), or compound of formula (I)+aminopyralid (CAS RN 150114-71-9)).

Mixtures of a compound of formula (I) with diflufenzopyr (252).

Mixtures of a compound of formula (I) with an acetanilide (e.g. compound of formula (I)+acetochlor (5), compound of formula (I)+dimethenamid (260), compound of formula (I)+metolachlor (548), compound of formula (I)+S-metolachlor (549), or compound of formula (I)+pretilachlor (656)).

Mixtures of a compound of formula (I) with flamprop-M (355).

Mixtures of a compound of formula (I) with flufenacet (BAY FOE 5043) (369).

Mixtures of a compound of formula (I) with pyroxasulfone (CAS RN 447399-55-5).

Mixtures of a compound of formula (I) with an HPPD inhibitor (e.g. compound of formula (I)+isoxaflutole (479), compound of formula (I)+mesotrione (515), compound of formula (I)+pyrasulfotole (CAS RN 365400-11-9), compound of formula (I)+sulcotrione (747), compound of formula (I)+tembotrione (CAS RN 335104-84-2), compound of formula (I)+topramezone (CAS RN 210631-68-8), compound of formula (I)+4-hydroxy-3-[[2-[(2-methoxyethoxy)methyl]-6-(trifluoromethyl)-3-pyridinyl]-carbonyl]-bicyclo[3.2.1]oct-3-en-2-one (CAS RN 352010-68-5), or compound of formula (I)+4-hydroxy-3-[[2-(3-methoxypropyl)-6-(difluoromethyl)-3-pyridinyl]-carbonyl]-bicyclo[3.2.1]oct-3-en-2-one (CAS RN 894355-80-7)).

Mixtures of a compound of formula (I) with a triazine (e.g. compound of formula (I)+atrazine (37), or compound of formula (I)+terbuthylazine (775)).

Mixtures of a compound of formula (I) with a triazine and an HPPD inhibitor (e.g. compound of formula (I)+triazine+isoxaflutole, compound of formula (I)+triazine+mesotrione, compound of formula (I)+triazine+pyrasulfotole, compound of formula (I)+triazine+sulcotrione, compound of formula (I)+triazine+tembotrione, compound of formula (I)+triazine+topramezone, compound of formula (I)+triazine+4-hydroxy-3-[[2-[(2-methoxyethoxy)-methyl]-6-(trifluoro-methyl)-3-pyridinyl]carbonyl]-bicyclo[3.2.1]oct-3-en-2-one, or compound of formula (I)+triazine+4-hydroxy-3-[[2-(3-methoxypropyl)-6-(difluoro-methyl)-3-pyridinyl]carbonyl]-bicyclo[3.2.1]oct-3-en-2-one).

Mixtures of a compound of formula (I) with glyphosate (419).

Mixtures of a compound of formula (I) with glyphosate and an HPPD inhibitor (e.g. compound of formula (I)+glyphosate+isoxaflutole, compound of formula (I)+glyphosate+mesotrione, compound of formula (I)+glyphosate+pyrasulfotole, compound of formula (I)+glyphosate+sulcotrione, compound of formula (I)+glyphosate+tembotrione, compound of formula (I)+glyphosate+topramezone, compound of formula (I)+glyphosate+4-hydroxy-3-[[2-[(2-methoxyethoxy)methyl]-6-(trifluoromethyl)-3-pyridinyl]carbonyl]-bicyclo[3.2.1]oct-3-en-2-one, or compound of formula (I)+glyphosate+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with glufosinate-ammonium (418).

Mixtures of a compound of formula (I) with glufosinate-ammonium and an HPPD inhibitor (e.g. compound of formula (I)+glufosinate-ammonium+isoxaflutole, compound of formula (I)+glufosinate-ammonium+mesotrione, compound of formula (I)+glufosinate-ammonium+pyrasulfotole, compound of formula (I)+glufosinate-ammonium+sulcotrione, compound of formula (I)+glufosinate-ammonium+tembotrione, compound of formula (I)+glufosinate-ammonium+topramezone, compound of formula (I)+glufosinate-ammonium+4-hydroxy-3-[[2-[(2-methoxy-ethoxy)methyl]-6-(trifluoromethyl)-3-pyridinyl]carbonyl]-bicyclo[3.2.1]oct-3-en-2-one, or compound of formula (I)+glufosinate-ammonium+4-hydroxy-3-[[2-(3-methoxypropyl)-6-(difluoromethyl)-3-pyridinyl]carbonyl]-bicyclo[3.2.1]oct-3-en-2-one).

Mixtures of a compound of formula (I) with an ALS or an AHAS inhibitor (e.g. compound of formula (I)+bensulfuron-methyl (64), compound of formula (I)+chlorimuron-ethyl (135), compound of formula (I)+cloransulam-methyl (164), compound of formula (I)+florasulam (359), compound of formula (I)+flucarbazone-sodium (364), compound of formula (I)+imazamox (451), compound of formula (I)+imazapyr (453), compound of formula (I)+imazethapyr (455), compound of formula (I)+iodosulfuron-methyl-sodium (466), compound of formula (I)+mesosulfuron-methyl (514), compound of formula (I)+nicosulfuron (577), compound of formula (I)+penoxsulam (622), compound of formula (I)+pyroxsulam (triflosulam) (CAS RN 422556-08-9), compound of formula (I)+thifensulfuron-methyl (thiameturon-methyl) (795), compound of formula (I)+triasulfuron (817), compound of formula (I)+tribenuron-methyl (822), compound of formula (I)+trifloxysulfuron-sodium (833), compound of formula (I)+thiencarbazone (4-[(4,5-dihydro-3-methoxy-4-methyl-5-oxo-1H-1,2,4-triazol-1-yl)carbonylsulfamoyl]-5-methylthiophene-3-carboxylic acid, BAY636)), or compound of formula (I)+thiencarbazone-methyl (methyl 4-[(4,5-dihydro-3-methoxy-4-methyl-5-oxo-1H-1,2,4-triazol-1-yl)carbonylsulfamoyl]-5-methylthiophene-3-carboxylate, CAS RN 317815-83-1, BAY636-methyl)).

Mixtures of a compound of formula (I) with a PPO inhibitor (e.g. compound of formula (I)+acifluorfen-sodium (7), compound of formula (I)+butafenacil (101), compound of formula (I)+carfentrazone-ethyl (121), compound of formula (I)+cinidon-ethyl (152), compound of formula (I)+flumioxazin (376), compound of formula (I)+fomesafen (401), compound of formula (I)+lactofen (486), or compound of formula (I)+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6)).

Mixtures of a compound of formula (I) with an ACCase inhibitor (e.g. compound of formula (I)+butroxydim (106), compound of formula (I)+clethodim (155), compound of formula (I)+clodinafop-propargyl (156), compound of formula (I)+cycloxydim (190), compound of formula (I)+cyhalofop-butyl (195), compound of formula (I)+diclofop-methyl (238), compound of formula (I)+fenoxaprop-P-ethyl (339), compound of formula (I)+fluazifop-butyl (361), compound of formula (I)+fluazifop-P-butyl (362), compound of formula (I)+haloxyfop (427), compound of formula (I)+haloxyfop-P (428), compound of formula (I)+propaquizafop (670), compound of formula (I)+quizalofop (717), compound of formula (I)+quizalofop-P (718), compound of formula (I)+sethoxydim (726), compound of formula (I)+tepraloxydim (771), compound of formula (I)+tralkoxydim (811)), or compound of formula (I)+pinoxaden (CAS RN 243973-20-8).

Mixtures of a compound of formula (I) with prosulfocarb (683), or a compound of formula (I) with tri-allate (816).

Mixtures of a compound of formula (I) with bromoxynil (95), a compound of formula (I) with chloridazon (134), a compound of formula (I) with chlorotoluron (143), a compound of formula (I) with diuron (281), or a compound of formula (I) with metribuzin (554).

Mixtures of a compound of formula (I) with clomazone (159), a compound of formula (I) with diflufenican (251), a compound of formula (I) with fluorochloridone (389), or a compound of formula (I) with flurtamone (392).

Mixtures of a compound of formula (I) with pendimethalin (621) or a compound of formula (I) with trifluralin (836).

Mixtures of a compound of formula (I) with difenzoquat metilsulfate (248).

Mixtures of a compound of formula (I) with diquat dibromide (276).

Mixtures of a compound of formula (I) with paraquat dichloride (614).

The mixing partners of the compound of formula (I) may also be in the form of esters or salts, as mentioned e.g. in The Pesticide Manual, 13th Edition (BCPC), 2003. The reference to glufosinate-ammonium also applies to glufosinate, the reference to cloransulam-methyl also applies to cloransulam, the reference to dimethenamid also applies to dimethenamid-P, the reference to flamprop-M also applies to flamprop, and the reference to pyrithiobac-sodium also applies to pyrithiobac, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

Additionally, one or more of the following herbicides or plant growth regulators can be used in combination with a compound of formula (I) according to the invention or in combination with a mixture as described above: aclonifen (8), acrolein (10), alachlor (14), alloxydim (18), ametryn (20), amicarbazone (21), amidosulfuron (22), aminocyclopyrachlor (CAS RN 858956-08-8), amitrole (aminotriazole) (25), ammonium sulfamate (26), anilofos (31), asulam (36), aviglycine (39), azafenidin (CAS RN 68049-83-2), azimsulfuron (43), BAS 800H(CAS RN 372137-35-4), beflubutamid (55), benazolin (57), bencarbazone (CAS RN 173980-17-1), benfluralin (59), benfuresate (61), bensulide (65), bentazone (67), benzfendizone (CAS RN 158755-95-4), benzobicyclon (69), benzofenap (70), bilanafos (bialaphos) (77), bispyribac-sodium (82), borax (86), bromacil (90), bromobutide (93), bromofenoxim (CAS RN 13181-17-4), butachlor (100), butamifos (102), butralin (105), butylate (108), cafenstrole (110), carbetamide (117), chlorbromuron (CAS RN 13360-45-7), chlorfurenol-methyl (133), chloroacetic acid (138), chlorpropham (144), chlorsulfuron (147), chlorthal-dimethyl (148), cinmethylin (153), cinosulfuron (154), clomeprop (160), cumyluron (180), cyanamide (182), cyanazine (183), cyclanilide (186), cycloate (187), cyclosulfamuron (189), daimuron (213), dalapon (214), dazomet (216), desmedipham (225), desmetryn (CAS RN 1014-69-3), dichlobenil (229), dichlorprop (234), dichlorprop-P (235), diclosulam (241), dimefuron (256), dimepiperate (257), dimethachlor (258), dimethamethryn (259), dimethipin (261), dimethylarsinic acid (264), dinitramine (268), dinoterb (272), dipropetryn (CAS RN 4147-51-7), dithiopyr (280), DNOC (282), DSMA (CAS RN 144-21-8), endothal (295), EPTC (299), esprocarb (303), ethalfluralin (305), ethametsulfuron-methyl (306), ethephon (307), ethofumesate (311), ethoxyfen (CAS RN 188634-90-4), ethoxyfen-ethyl (CAS RN 131086-42-5), ethoxysulfuron (314), etobenzanid (318), fentrazamide (348), ferrous sulfate (353), flazasulfuron (356), fluazolate (isopropazol) (CAS RN 174514-07-9), flucetosulfuron (CAS RN 412928-75-7), fluchloralin (365), flufenpyr-ethyl (371), flumetralin (373), flumetsulam (374), flumiclorac-pentyl (375), flumipropyn (flumipropin) (CAS RN 84478-52-4), fluometuron (378), fluoroglycofen-ethyl (380), flupoxam (CAS RN 119126-15-7), flupropacil (CAS RN 120890-70-2), flupropanate (383), flupyrsulfuron-methyl-sodium (384), flurenol (387), fluridone (388), fluoroxypyr (390), fluthiacet-methyl (395), foramsulfuron (402), fosamine (406), halosulfuron-methyl (426), HC-252 (429), hexazinone (440), imazamethabenz-methyl (450), imazapic (452), imazaquin (454), imazosulfuron (456), indanofan (462), ioxynil (467), isoproturon (475), isouron (476), isoxaben (477), isoxachlortole (CAS RN 141112-06-3), isoxapyrifop (CAS RN 87757-18-4), karbutilate (482), lenacil (487), linuron (489), MCPA-thioethyl (500), MCPB (501), mecoprop (503), mecoprop-P (504), mefenacet (505), mefluidide (507), metam (519), metamifop (mefluoxafop) (520), metamitron (521), metazachlor (524), methabenzthiazuron (526), methazole (CAS RN 20354-26-1), methylarsonic acid (536), 1-methylcyclopropene (538), methyldymron (539), methyl isothiocyanate (543), metobenzuron (547), metobromuron (CAS RN 3060-89-7), metosulam (552), metoxuron (553), metsulfuron-methyl (555), MK-616 (559), molinate (560), monolinuron (562), MSMA (CAS RN 2163-80-6), naproanilide (571), napropamide (572), naptalam (573), neburon (574), nipyraclofen (CAS RN 99662-11-0), n-methyl-glyphosate, nonanoic acid (583), norflurazon (584), oleic acid (fatty acids) (593), orbencarb (595), orthosulfamuron (CAS RN 213464-77-8), oryzalin (597), oxadiargyl (599), oxadiazon (600), oxasulfuron (603), oxaziclomefone (604), oxyfluorfen (610), pebulate (617), pentachlorophenol (623), pentanochlor (624), pentoxazone (625), pethoxamid (627), petrolium oils (628), phenmedipham (629), picloram (645), picolinafen (646), piperophos (650), primisulfuron-methyl (657), prodiamine (661), profluazol (CAS RN 190314-43-3), profoxydim (663), prohexadione calcium (664), prometon (665), prometryn (666), propachlor (667), propanil (669), propazine (672), propham (674), propisochlor (667), propoxycarbazone-sodium (procarbazone-sodium) (679), propyzamide (681), prosulfuron (684), pyraclonil (pyrazogyl) (CAS RN 158353-15-2), pyraflufen-ethyl (691), pyrazolynate (692), pyrazosulfuron-ethyl (694), pyrazoxyfen (695), pyribenzoxim (697), pyributicarb (698), pyridafol (CAS RN 40020-01-7), pyridate (702), pyriftalid (704), pyriminobac-methyl (707), pyrimisulfan (CAS RN 221205-90-9), pyrithiobac-sodium (709), quinmerac (713), quinoclamine (714), rimsulfuron (721), sequestrene, siduron (727), simazine (730), simetryn (732), sodium chlorate (734), sulfentrazone (749), sulfometuron-methyl (751), sulfosate (CAS RN 81591-81-3), sulfosulfuron (752), sulfuric acid (755), tar oils (758), TCA-sodium (760), tebutam (CAS RN 35256-85-0), tebuthiuron (765), tefuryltrione (CAS RN 473278-76-1), terbacil (772), terbumeton (774), terbutryn (776), thenylchlor (789), thidiazimin (CAS RN 123249-43-4), thiazafluoron (CAS RN 25366-23-8), thiazopyr (793), thiobencarb (797), tiocarbazil (807), triaziflam (819), triclopyr (827), trietazine (831), triflusulfuron-methyl (837), trihydroxytriazine (CAS RN 108-80-5), trinexapac-ethyl (CAS RN 95266-40-3), tritosulfuron (843), N-[(1R,2S)-2,6-dimethyl-2,3-dihydro-1H-inden-1-yl]-6-(1-fluoroethyl)-1,3,5-triazine-2,4-diamine (CAS RN 950782-86-2), 1-(2-chloro-6-propylimidazo[1,2-b]pyridazin-3-ylsulfonyl)-3-(4,6-dimethoxypyrimidin-2-yl)urea (CAS RN 570415-88-2), and 5-(2,6-difluoro-benzyloxymethyl)-5-methyl-3-(3-methyl-thiophen-2-yl)-4,5-dihydro-isoxazole (CAS RN 403640-27-7).

The mixing partners of the compound of formula (I) may also be in the form of esters or salts, as mentioned e.g. in The Pesticide Manual, 13th Edition (BCPC), 2003. The reference to acifluorfen-sodium also applies to acifluorfen, and the reference to bensulfuron-methyl also applies to bensulfuron, etc.

The mixing ratio of the compound of formula (I) to the mixing partner is preferably from 1:100 to 1000:1.

The mixtures can advantageously be used in the above-mentioned formulations (in which case "active ingredient" relates to the respective mixture of compound of formula (I) with the mixing partner).

The compounds of formula (I) according to the invention can also be used in combination with one or more safeners. Likewise, mixtures of a compound of formula (I) according to the invention with one or more further herbicides can also be used in combination with one or more safeners. The term "safener" as used herein means a chemical that when used in combination with a herbicide reduces the undesirable effects of the herbicide on non-target organisms, for example, a safener protects crops from injury by herbicides but does not prevent the herbicide from killing the weeds. The safeners can be AD-67 (11), benoxacor (63), cloquintocet-mexyl (163), cyometrinil (CAS RN 78370-21-5), cyprosulfamide (CAS RN 221667-31-8), dichlormid (231), dicyclonon (CAS RN 79260-71-2), fenchlorazole-ethyl (331), fenclorim (332), flurazole (386), fluxofenim (399), furilazole (413) and the corresponding R isomer, isoxadifen-ethyl (478), mefenpyr-diethyl (506), 2-methoxy-N-[[4-[[(methylamino)carbonyl] amino]-phenyl]sulfonyl]-benzamide (CAS RN 129531-12-0), naphthalic anhydride (CAS RN 81-84-5), and oxabetrinil (598). Particularly preferred are mixtures of a compound of formula (I) with benoxacor and a compound of formula (I) with cloquintocet-mexyl.

The safeners of the compound of formula (I) may also be in the form of esters or salts, as mentioned e.g. in The Pesticide Manual, 13th Edition (BCPC), 2003. The reference to cloquintocet-mexyl also applies to cloquintocet, and the reference to fenchlorazole-ethyl also applies to fenchlorazole, etc.

Preferably the mixing ratio of compound of formula (I) to safener is from 100:1 to 1:10, especially from 20:1 to 1:1.

The mixtures can advantageously be used in the above-mentioned formulations (in which case "active ingredient" relates to the respective mixture of compound of formula (I) with the safener). It is possible that the safener and a compound of formula (I) and one or more additional herbicide(s), if any, are applied simultaneously. For example, the safener, a compound of formula (I) and one or more additional herbicide(s), if any, might be applied to the locus pre-emergence or might be applied to the crop post-emergence. It is also possible that the safener and a compound of formula (I) and one or more additional herbicide(s), if any, are applied sequentially. For example, the safener might be applied before sowing the seeds as a seed treatment and a compound of formula (I) and one or more additional herbicides, if any, might be applied to the locus pre-emergence or might be applied to the crop post-emergence.

Preferred mixtures of a compound of formula (I) with further herbicides and safeners include:

Mixtures of a compound of formula (I) with S-metolachlor and a safener, particularly benoxacor.

Mixtures of a compound of formula (I) with isoxaflutole and a safener.

Mixtures of a compound of formula (I) with mesotrione and a safener.

Mixtures of a compound of formula (I) with sulcotrione and a safener.

Mixtures of a compound of formula (I) with a triazine and a safener.

Mixtures of a compound of formula (I) with a triazine and isoxaflutole and a safener.

Mixtures of a compound of formula (I) with a triazine and mesotrione and a safener.

Mixtures of a compound of formula (I) with a triazine and sulcotrione and a safener.

Mixtures of a compound of formula (I) with glyphosate and a safener.

Mixtures of a compound of formula (I) with glyphosate and isoxaflutole and a safener.

Mixtures of a compound of formula (I) with glyphosate and mesotrione and a safener.

Mixtures of a compound of formula (I) with glyphosate and sulcotrione and a safener.

Mixtures of a compound of formula (I) with glufosinate-ammonium and a safener.

Mixtures of a compound of formula (I) with glufosinate-ammonium and isoxaflutole and a safener.

Mixtures of a compound of formula (I) with glufosinate-ammonium and mesotrione and a safener.

Mixtures of a compound of formula (I) with glufosinate-ammonium and sulcotrione and a safener.

Mixtures of a compound of formula (I) with florasulam and a safener, particularly cloquintocet-mexyl.

Mixtures of a compound of formula (I) with clodinafop-propargyl and a safener, particularly cloquintocet-mexyl.

Mixtures of a compound of formula (I) with pinoxaden and a safener, particularly cloquintocet-mexyl.

Mixtures of a compound of formula (I) with bromoxynil and a safener, particularly cloquintocet-mexyl.

The following Examples further illustrate, but do not limit, the invention.

PREPARATION EXAMPLES

The following abbreviations were used throughout this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl.

1. Reactions which are Covered by Scheme 1

Example 1.1

Preparation of 2-amino-nicotinic acid methyl ester

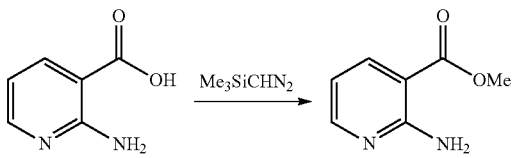 [SMILES: Nc1ncccc1C(=O)O ; COC(=O)c1cccnc1N]

To a solution of 3-amino-pyridine-2-carboxylic acid (1 g) in methanol (8 ml) and toluene (10 ml), under nitrogen atmosphere, was added a solution of (trimethylsilyl)-diazomethane (3.625 ml) (2M in diethylether). When the effervescence from the reaction had subsided a further portion of (trimethylsilyl)diazomethane (3.625 ml) (2M in diethylether) was added. The reaction mixture was stirred at ambient temperature for 20 hours. The reaction was quenched by addition of acetic acid (0.2 ml). The mixture was concentrated and the residue partitioned between dichloromethane and aqueous potassium carbonate (5% by weight). The phases were separated and the aqueous phase was extracted with further dichloromethane. The combined organic extracts were dried over magnesium sulfate and concentrated to give 2-amino-nicotinic acid methyl ester as a light yellow solid (968 mg). 1H-NMR (400 MHz, CDCl$_3$): 8.21-8.23 (m, 1H), 8.12-8.14 (m, 1H), 6.61-6.64 (m, 1H), 3.89 (s, 3H) ppm.

The following compounds made were made using analogous procedures.

2-Amino-6-chloro-nicotinic acid methyl ester. 1H-NMR (400 MHz, CDCl$_3$): 8.03-8.05 (d, 1H), 6.59-6.61 (d, 1H), 3.88 (s, 3H) ppm.

3-Amino-pyridine-2-carboxylic acid methyl ester. 1H-NMR (400 MHz, CDCl$_3$): 8.07-8.08 (m, 1H), 7.21-7.24 (m, 1H), 7.04-7.07 (m, 1H), 5.76 (bs, 2H), 3.98 (s, 3H), ppm.

Example 1.2

Preparation of 2-[2-(2,4-dichloro-phenyl)-acetylamino]-nicotinic acid methyl ester

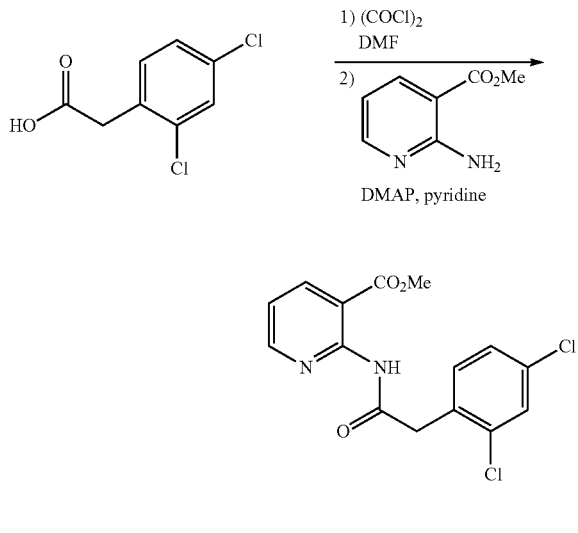

Oxalyl chloride (0.14 ml) was added dropwise to a solution of (2,4-dichloro-phenyl)-acetic acid (270 mg) in dichloromethane (10 ml) at ambient temperature. A drop of N,N-dimethylformamide ("DMF") was added to initiate the reaction. The reaction mixture was stirred at ambient temperature for 2 hours. The reaction mixture was concentrated to give a colourless oil which was dissolved in dichloromethane (3 ml). The mixture was added dropwise to a cooled (−5° C.) slurry of 2-amino-nicotinic acid methyl ester (200 mg) (Example 1.1), 4-dimethylaminopyridine ("DMAP") (32 mg) and pyridine (0.19 ml) in dichloromethane (5 ml). The reaction mixture was allowed to warm to ambient temperature and stirred at ambient temperature for 16 hours. The reaction mixture was partitioned between dichloromethane and aqueous hydrochloric acid (2M). The phases were separated. The organic layer was dried over magnesium sulfate and concentrated. The residue was purified by column chromatography on silica gel (eluent: acetone/iso-hexane ratio 1:9 to 2:8) to give 2-[2-(2,4-dichloro-phenyl)-acetylamino]-nicotinic acid methyl ester as a light yellow gum (197 mg). 1H-NMR (400 MHz, CDCl$_3$): 10.81 (bs, 1H), 8.59-8.60 (m, 1H), 8.29-8.31 (m, 1H), 7.42-7.44 (m, 1H), 7.34-7.36 (m, 1H), 7.23-7.27 (m, 1H), 7.07-7.11 (m, 1H), 4.08 (s, 2H), 3.90 (s, 3H) ppm.

The following compounds made were made using analogous procedures.

2-[2-(2,6-Dichloro-phenyl)-acetylamino]-nicotinic acid methyl ester. 1H-NMR (400 MHz, CDCl$_3$): 10.74 (bs, 1H), 8.59-8.61 (m, 1H), 8.28-8.31 (m, 1H), 7.33-7.38 (m, 2H), 7.19-7.23 (m, 1H), 7.06-7.09 (m, 1H), 4.41 (s, 2H), 3.89 (s, 3H) ppm.

2-[2-(2-Trifluoromethoxy-phenyl)-acetylamino]-nicotinic acid methyl ester. 1H-NMR (400 MHz, CDCl$_3$): 10.76 (bs, 1H), 8.57-8.59 (m, 1H), 8.27-8.29 (m, 1H), 7.46-7.48 (m, 1H), 7.26-7.36 (m, 3H), 7.05-7.09 (m, 1H), 4.03 (s, 2H), 3.88 (s, 3H) ppm.

2-[2-(2-Chloro-3,6-difluoro-phenyl)-acetylamino]-nicotinic acid methyl ester. 1H-NMR (400 MHz, CDCl$_3$): 10.88 (bs, 1H), 8.59-8.60 (m, 1H), 8.31-8.33 (m, 1H), 6.98-7.14 (m, 3H), 4.27 (s, 2H), 3.91 (s, 3H) ppm.

2-[2-(2,6-Diethyl-4-methyl-phenyl)-acetylamino]-nicotinic acid methyl ester. 1H-NMR (400 MHz, CDCl$_3$): 10.16 (bs, 1H), 8.59-8.61 (m, 1H), 8.21-8.23 (dd, 1H), 7.04-7.07 (m, 1H), 6.97 (s, 2H), 3.94 (s, 2H), 3.78 (s, 3H), 2.62-2.70 (m, 4H), 2.34 (s, 3H), 1.18-1.23 (t, 6H) ppm.

5-Bromo-2-[2-(2-chloro-3,6-difluoro-phenyl)-acetylamino]-nicotinic acid. 1H-NMR (400 MHz, CDCl$_3$): 8.97 (d, 1H), 8.62-8.63 (d, 1H), 7.12-7.18 (m, 1H), 7.03-7.08 (m, 1H), 4.31 (s, 2H) ppm.

6-Chloro-2-[2-(2-chloro-3,6-difluoro-phenyl)-acetylamino]-nicotinic acid methyl ester. 1H-NMR (400 MHz, CDCl$_3$): 10.88 (bs, 1H), 8.23-8.25 (d, 1H), 7.05-7.11 (m, 1H), 7.05-7.07 (d, 1H), 6.96-7.03 (m, 1H), 4.34 (s, 2H), 3.92 (s, 3H) ppm.

3-[2-(2,4-Dichloro-phenyl)-acetylamino]-pyridine-2-carboxylic acid methyl ester. 1H-NMR (400 MHz, CDCl$_3$): 11.04 (bs, 1H), 9.09-9.11 (dd, 1H), 8.42-8.43 (dd, 1H), 7.47-7.50 (m, 2H), 7.29-7.37 (m, 2H), 3.99 (s, 3H), 3.91 (s, 2H) ppm.

3-[2-(2-Trifluoromethoxy-phenyl)-acetylamino]-pyridine-2-carboxylic acid methyl ester. 1H-NMR (400 MHz, CDCl$_3$): 11.04 (bs, 1H), 9.10 (dd, 1H), 8.41 (dd, 1H), 7.30-7.50 (m, 5H), 3.90 (s, 3H), 3.89 (s, 2H) ppm.

3-[2-(2-Chloro-3,6-difluoro-phenyl)-acetylamino]-pyridine-2-carboxylic acid methyl ester. 1H-NMR (400 MHz, CDCl$_3$): 11.09 (bs, 1H), 9.08-9.09 (dd, 1H), 8.42-8.43 (dd, 1H), 7.46-7.50 (m, 1H), 7.05-7.18 (m, 2H), 4.03 (s, 2H), 3.99 (s, 3H) ppm.

3-[2-(2,6-Diethyl-4-methyl-phenyl)-acetylamino]-pyridine-2-carboxylic acid methyl ester. 1H-NMR (400 MHz, CDCl$_3$): 10.62 (bs, 1H), 9.10-9.12 (dd, 1H), 8.38-8.39 (dd, 1H), 7.44-7.47 (m, 1H), 6.98 (s, 2H), 3.88 (s, 3H), 3.87 (s, 2H), 2.63-2.68 (q, 4H), 2.35 (s, 3H), 1.21 (t, 6H) ppm.

4-[2-(2-Chloro-3,6-difluoro-phenyl)-acetylamino]-nicotinic acid methyl ester. 1H-NMR (400 MHz, CDCl$_3$): 11.27 (bs, 1H), 9.15 (s, 1H), 8.60 (s, 2H), 7.13-7.19 (m, 1H), 7.05-7.11 (m, 1H), 4.04 (s, 2H), 3.94 (s, 3H) ppm.

3-[2-(2-Chloro-3,6-difluoro-phenyl)-acetylamino]-isonicotinic acid ethyl ester. 1H-NMR (400 MHz, CDCl$_3$): 10.80 (bs, 1H), 10.00 (s, 1H), 8.44 (d, 1H), 7.79-7.80 (d, 1H), 7.12-7.18 (m, 1H), 7.05-7.11 (m, 1H), 4.41-4.55 (q, 2H), 4.04 (s, 2H), 1.40-1.43 (t, 3H) ppm.

6-[2-(2-Chloro-3,6-difluoro-phenyl)-acetylamino]-[1,2,4]triazine-5-carboxylic acid ethyl ester. 1H-NMR (400 MHz, CDCl$_3$): 10.14 (bs, 1H), 9.64 (s, 1H), 7.12-7.17 (m, 1H), 7.02-7.08 (m, 1H), 4.47-4.52 (q, 2H), 4.31 (s, 2H), 1.45 (t, 3H) ppm.

4-[2-(2-Chloro-3,6-difluoro-phenyl)-acetylamino]-pyrimidine-5-carboxylic acid methyl ester. 1H-NMR (400 MHz, CDCl$_3$): 10.94 (bs, 1H), 9.19 (s, 1H), 9.06 (s, 1H), 7.00-7.15 (m, 2H), 4.40 (s, 2H), 3.98 (s, 3H) ppm.

2-[2-(2-Chloro-3,6-difluoro-phenyl)-acetylamino]-6-trifluoromethyl-nicotinic acid methyl ester. 1H-NMR (400 MHz, CDCl$_3$): 10.82 (bs, 1H), 8.52 (d, 1H), 7.07-7.13 (m, 1H), 6.99-7.04 (m, 1H), 4.46 (s, 2H), 3.99 (s, 3H) ppm.

2-[2-(3-Bromo-2-chloro-6-fluoro-phenyl)-acetylamino]-nicotinic acid methyl ester. 1H-NMR (400 MHz, CDCl$_3$): 10.84 (bs, 1H), 8.57-8.58 (d, 1H), 8.30 (d, 1H), 7.55-7.58 (m, 1H), 7.06-7.09 (m, 1H), 6.94-6.97 (m, 1H), 4.33 (s, 2H), 3.91 (s, 3H) ppm.

2-{[2-(2,3-Dichloro-6-fluoro-phenyl)-acetyl]-ethylamino}-4-methoxy-nicotinic acid ethyl ester. 1H-NMR (400 MHz, CDCl$_3$): 8.56-8.57 (d, 1H), 7.30-7.34 (m, 1H), 6.96-7.00 (m, 1H), 6.90-6.93 (d, 1H), 4.39-4.44 (q, 2H), 3.97 (s, 3H) 3.90-3.96 (m, 2H), 3.67 (s, 2H), 1.35-1.39 (t, 3H), 1.14-1.18 (t, 3H) ppm.

Example 1.3

Preparation of 2-(2-pyridin-2-yl-acetylamino)-nicotinic acid methyl ester

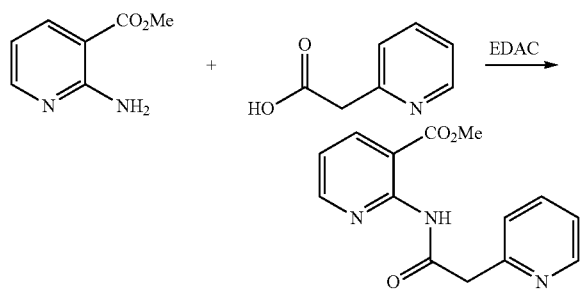

To a solution of 2-pyridyl-acetic acid hydrochloride (310 mg) and 2-amino-nicotinic acid methyl ester (270 mg) (Example 1.1) in dichloromethane (5 ml) was added diisopropylethylamine (0.32 ml). The reaction mixture was stirred at ambient temperature for 20 minutes. To this solution was added 4-dimethylaminopyridine (43 mg) and N-(3-dimethylaminopropyl)-N'-ethylcarbodiimide hydrochloride ("EDAC") (410 mg). The reaction mixture was stirred at ambient temperature for 20 hours. The reaction mixture was partitioned between dichloromethane and water. The phases were separated and the organic layer concentrated. The residue was purified by column chromatography on silica gel (eluent: 15% acetone in dichloromethane) to give 2-(2-pyridin-2-yl-acetylamino)-nicotinic acid methyl ester as a yellow solid (86 mg). 1H-NMR (400 MHz, CDCl$_3$): 11.14 (bs, 1H), 8.63-8.64 (m, 1H), 8.58-8.59 (dd, 1H), 8.25-8.27 (dd, 1H), 7.66-7.70 (m, 1H), 7.38 (d, 1H), 7.20-7.23 (m, 1H), 7.05-7.08 (dd, 1H), 4.11 (s, 2H), 3.92 (s, 3H) ppm.

The following compounds were made using analogous procedures:

3-(2-Pyridin-2-yl-acetylamino)-pyridine-2-carboxylic acid methyl ester. 1H-NMR (400 MHz, CDCl$_3$): 11.36 (bs, 1H), 9.10-9.12 (dd, 1H), 8.67-8.69 (m, 1H), 8.40-8.41 (dd, 1H), 7.69-7.73 (m, 1H), 7.45-7.48 (m, 1H), 7.36-7.37 (m, 1H), 7.24-7.27 (m, 1H), 4.01 (s, 3H), 4.00 (s, 2H) ppm.

Example 1.4

Preparation of 3-(2,4-dichloro-phenyl)-4-hydroxy-1H-[1,8]naphthyridin-2-one (Compound D1 of Table D)

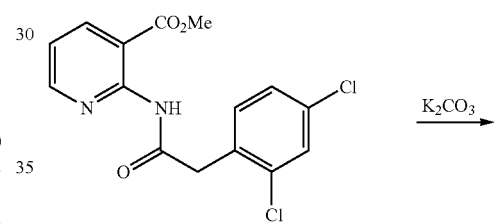

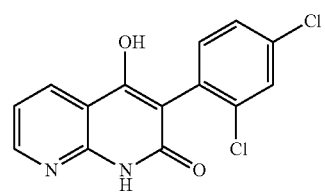

A mixture of 2-[2-(2,4-dichloro-phenyl)-acetylamino]-nicotinic acid methyl ester (190 mg) (Example 1.2) and potassium carbonate (1 g) in N,N-dimethylformamide (5 ml) was heated to 110° C. for 5 hours. The reaction mixture was allowed to cool to ambient temperature and then stored at ambient temperature for 16 hours. Water (5 ml) was added to the reaction mixture and the mixture acidified with potassium hydrogen sulfate (1M in water). The precipitate was isolated and washed successively with water and diethylether and dried to give Compound D1 of Table D as a beige solid (74 mg).

The following compounds made were made using analogous procedures:

6-(2-Chloro-3,6-difluoro-phenyl)-5-hydroxy-8H-pyrido[2,3-d]pyrimidin-7-one. 1H-NMR (400 MHz, d$_6$-DMSO): 10.97 (bs, 1H), 8.93 (s, 1H), 8.78 (s, 1H), 7.26-7.32 (m, 1H), 7.12-7.18 (m, 1H) ppm.

Compound Nos. A1, A2 and A8 of Table A, Compound No. B2 of Table B, Compound Nos. D2, D3, D4, D12, D14 and D33 of Table D and Compound No. E4 of Table E.

Example 1.5

Preparation of 4-Hydroxy-3-pyridin-3-yl-1H-[1,8]naphthyridin-2-one (Compound No. D11 of Table D)

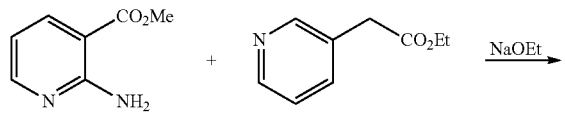

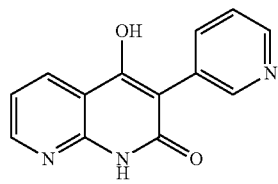

To a solution of 2-amino-nicotinic acid methyl ester (200 mg) (Example 1.1) in N,N-dimethylformamide ("DMF") (2 ml) was added sodium ethoxide (21 µl) (21% by weight in ethanol) followed by ethyl-3-pyridyl-acetate (200 µl). The reaction mixture was heated in the microwave at 150° C. for 15 minutes. The mixture was quenched by addition of aqueous hydrochloric acid (2M) (0.72 ml) and then diluted with water. The precipitate was isolated by filtration and washed with water and finally triturated with diethyl ether to give 4-hydroxy-3-pyridin-3-yl-1H-[1,8]naphthyridin-2-one as a beige solid (109 mg). 1H-NMR (400 MHz, $d_6$-DMSO): 11.75 (bs, 1H), 8.70 (m, 1H), 8.52-8.53 (dd, 1H), 8.48-8.49 (dd, 1H), 8.35-8.37 (dd, 1H), 7.98 (d, 1H), 7.45-7.49 (dd, 1H), 7.23-7.26 (dd, 1H) ppm.

The following compound was made using an analogous procedure:

Compound No. A7 of Table A.

Example 1.6

Preparation of 2,2-dimethyl-propionic acid 3-(2-chloro-3,6-difluoro-phenyl)-2-oxo-1,2-dihydro-[1,8]naphthyridin-4-yl ester

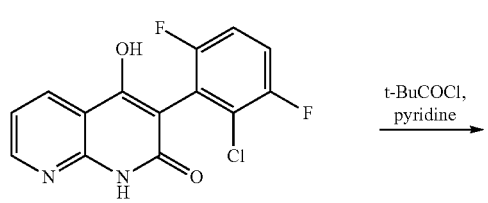

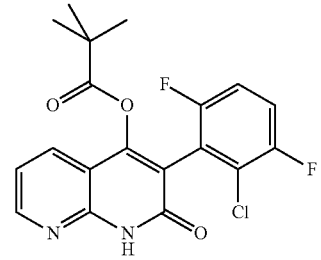

Compound D4 of Table D (1.487 g) and pyridine (0.978 ml) were stirred in dichloromethane (30 ml) at ambient temperature for 5 minutes. 2,2-Dimethylpropionyl chloride (0.21 ml) was added portionwise over a period of 10 minutes and the reaction stirred at ambient temperature for a further 3 hours. The reaction mixture was diluted with dichloromethane and washed successively with water, aqueous sodium hydrogen carbonate (1M) and aqueous hydrochloric acid (2M). The organic layer was dried over magnesium sulfate and concentrated. The residue was purified by column chromato-graphy on silica gel (eluent: ethyl acetate/hexane 1:1) to give 2,2-dimethyl-propionic acid 3-(2-chloro-3,6-difluoro-phenyl)-2-oxo-1,2-dihydro-[1,8]naphthyridin-4-yl ester as a white solid (764 mg). 1H-NMR (400 MHz, CDCl$_3$): 11.61 (bs, 1H), 8.80-8.81 (d, 1H), 7.85-7.87 (d, 1H), 7.29-7.30 (d, 1H), 7.19-7.24 (m, 1H), 7.06-7.10 (m, 1H), 1.16 (s, 9H) ppm.

The following compounds were made using analogous procedures:

Isobutyric acid 3-(3-bromo-2-chloro-6-fluoro-phenyl)-2-hydroxy-[1,8]naphthyridin-4-yl ester. 1H-NMR (400 MHz, CDCl$_3$): 12.04 (bs, 1H), 8.82-8.84 (d, 1H), 7.89-7.91 (d, 1H), 7.67-7.71 (m, 1H), 7.26-7.30 (m, 1H), 7.01-7.05 (t, 1H), 2.71 (sept, 1H), 1.08-1.09 (d, 3H), 1.06-1.07 (d, 3H) ppm.

Compound No. B3 of Table B, Compound No. D15 of Table D, Compound Nos. E1 and E5 of Table E.

2. Reactions which are Covered by Scheme 2

Example 2.1

Preparation of 3-(2-chloro-3,6-difluoro-phenyl)-1-(2,2-difluoro-ethyl)-4-hydroxy-1H-[1,8]naphthyridin-2-one (Compound No. D21 of Table D)

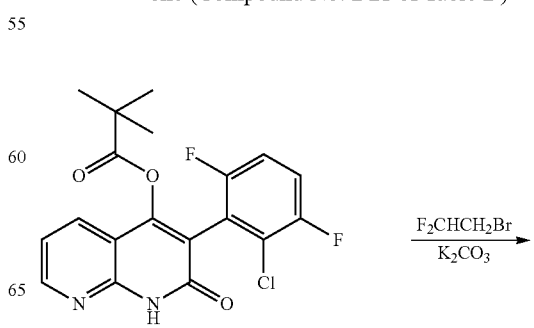

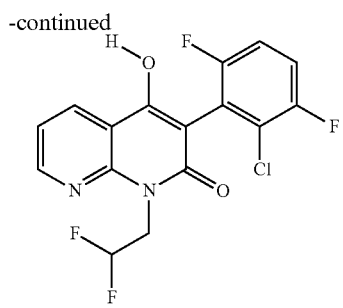

A mixture of 2,2-dimethyl-propionic acid 3-(2-chloro-3,6-difluoro-phenyl)-2-oxo-1,2-dihydro-[1,8]naphthyridin-4-yl ester (Example 1.5) (0.2 g), potassium carbonate (0.211 g) and 1-bromo-2,2-difluoro-ethane (0.15 g) in N,N-dimethylformamide (3 ml) was heated to 120° C. in a microwave for 15 minutes. The reaction mixture was partitioned between ethyl acetate and water. The phases were separated and the organic phase was dried over magnesium sulfate and concentrated. The residue was purified by column chromatography on silica gel (eluent: ethyl acetate/hexane 1:1) to give Compound No. D21 of Table D as a colourless oil (24 mg).

The following compounds made were made using analogous procedures: Compound Nos. D17 and D32 of Table D and Compound No. E6 of Table E.

Example 2.2

Preparation of isobutyric acid 3-(2,6-diethyl-4-methyl-phenyl)-1-methyl-2-oxo-1,2-dihydro-[1,8]naphthyridin-4-yl ester (Compound No. D6 of Table D)

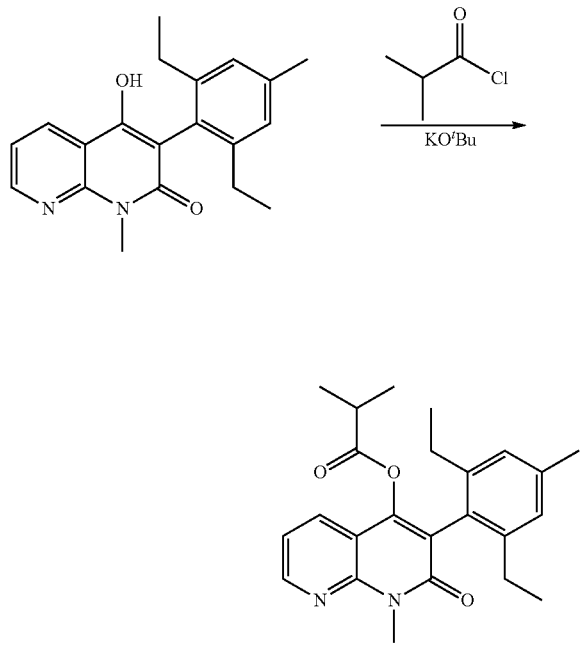

To a solution of Compound No. D23 of Table D (100 mg) (Example 3.2) in tetrahydrofuran (5 ml) was added potassium tert-butoxide (0.38 ml) (1M in tetrahydrofuran). The reaction mixture was stirred at ambient temperature for 30 minutes. To this mixture was added isobutyryl chloride (42 µl) and the reaction mixture stirred for at ambient temperature 2 hours. The reaction mixture was concentrated and the residue purified by column chromatographed on silica gel (eluent: 1% ethyl acetate/dichloromethane) to give Compound No. D6 of Table D as a white solid (110 mg).

The following compounds made were made using analogous procedures: Compound Nos. A4 to A6 of Table A and Compound Nos. D7 to D9 of Table D.

Example 2.3

Preparation of 2,2-dimethyl-propionic acid 3-(2-chloro-3,6-difluoro-phenyl)-1-(2,2-difluoro-ethyl)-2-oxo-1,2-dihydro-[1,8]naphthyridin-4-yl ester (Compound No. D10 of Table D)

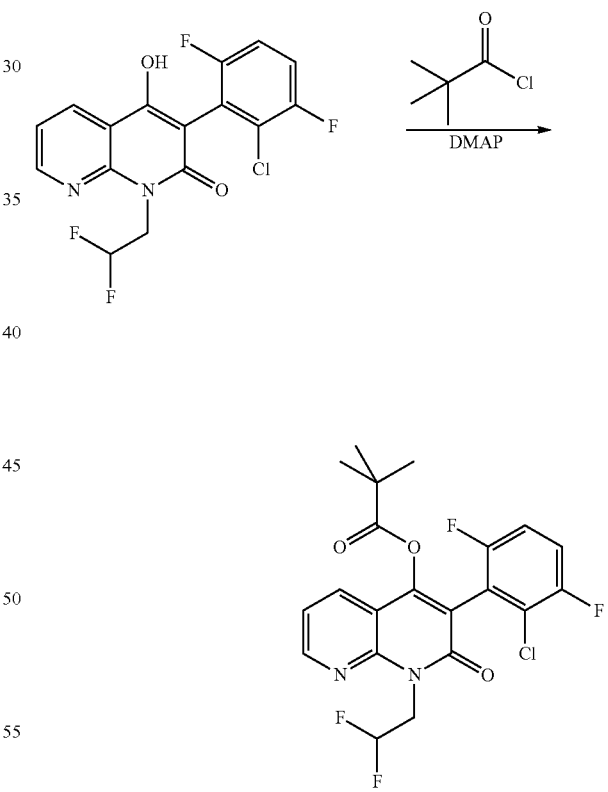

To a solution of Compound No. D24 of Table D (Example 2.1) (300 mg) in acetonitrile (3 ml) was added 4-dimethylaminopyridine ("DMAP") (10 mg) and 2,2-dimethyl-propionyl chloride (0.21 ml). The reaction mixture was heated in a microwave for 1500 seconds at 150° C. The reaction mixture was concentrated and the residue purified by column chromatography on silica gel (eluent: ethyl acetate/hexane 1:4) to give Compound No. D10 of Table D (24 mg).

The following compounds made were made using analogous procedures: Compound No. B5 of Table B, Compound No. C2 of Table C, Compound Nos. D16 and D19 of Table D.

Example 2.4

Preparation of 2,2-dimethyl-propionic acid 3-(2-chloro-3,6-difluoro-phenyl)-1-ethyl-2-oxo-1,2-dihydro-[1,6]naphthyridin-4-yl ester (Compound No. B1 of Table B)

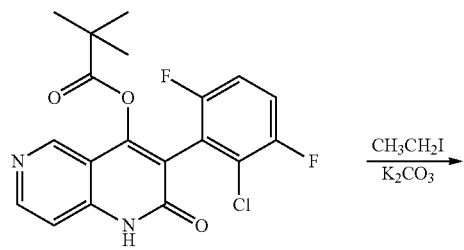

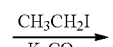

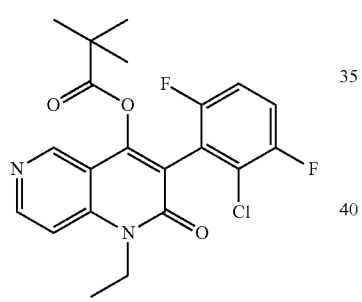

To a solution of 2,2-dimethyl-propionic acid 3-(2-chloro-3,6-difluoro-phenyl)-2-oxo-1,2-dihydro-[1,6]naphthyridin-4-yl ester (250 mg) in acetonitrile (1.5 ml) was added potassium carbonate (88 mg) followed by methyl iodide (51 µl). The reaction mixture was heated to 100° C. for 22 minutes in a microwave and then cooled to ambient temperature. The reaction mixture was diluted with ethyl acetate and water. The phases were separated. The organic fraction was washed with water and brine, dried over magnesium sulfate and concentrated. The residue was purified by column chromatography on silica gel (eluent: ethyl acetate/hexane 1:3 and then 1:1) to give Compound No. B1 of Table B as an orange oil (16 mg). 1H-NMR (400 MHz, CDCl$_3$): 8.84 (s, 1H), 8.71 (d, 1H), 7.32 (d, 1H), 7.18-7.23 (m, 1H), 7.05-7.10 (m, 1H), 4.38 (q, 2H), 1.41 (t, 3H), 1.16 (s, 9H) ppm.

The following compounds made were made using analogous procedures: Compound No. D30 of Table D, and Compound Nos. E2 and E3 of Table E. Furthermore, Compound No. D31 of Table D was isolated as a by-product of Compound No. D30 of Table D.

Example 2.5

Preparation of isobutyric acid 3-(3-bromo-2-chloro-6-fluoro-phenyl)-1-(2,2-difluoro-ethyl)-2-oxo-1,2-dihydro-[1,8]naphthyridin-4-yl ester (Compound No. D23 of Table D)

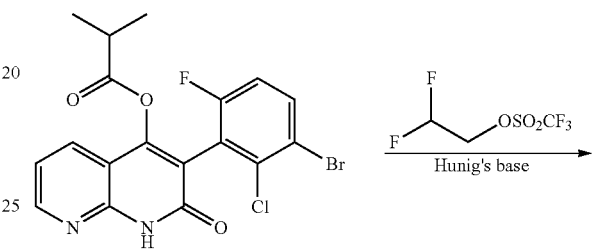

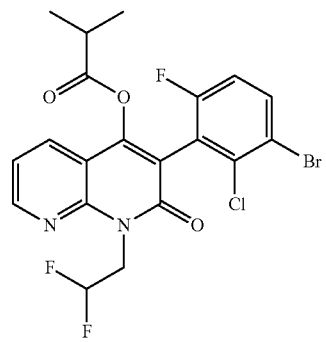

To a solution of Isobutyric acid 3-(3-bromo-2-chloro-6-fluoro-phenyl)-2-hydroxy-[1,8]naphthyridin-4-yl ester (1.749 g) in acetonitrile (17 ml) was added N,N-diisopropylethylamine ("Hunig's base") (0.83 ml) at ambient temperature. The mixture was stirred for 5 minutes at ambient temperature before drop wise addition of a solution of 2,2-difluoroethyltrifluoromethanesulfonate (1.022 g) at ambient temperature. The reaction mixture was stirred at ambient temperature for 7 hours when further 2,2-difluoroethyltrifluoromethanesulfonate (0.5 g) and the reaction was stirred overnight. A further portion of 2,2-difluoroethyltrifluoromethanesulfonate (0.5 g) and N,N-diisopropylethylamine ("Hunig's base") (0.83 ml) was added and the reaction was stirred for 5 hours then left to stand overnight. The reaction was concentrated and partitioned between ethyl acetate and 2M hydrochloric acid. The organic layer was dried and concentrated and the oily residue was purified by column chromatography on silica (eluent: 4:1 hexane:ethyl acetate) to give Compound No. D23 of Table D as a light yellow solid (1.56 g).

3. Reactions which are Covered by Scheme 3

Example 3.1

Preparation of 2-{[2-(2,6-diethyl-4-methyl-phenyl)-acetyl]-methyl-amino}-nicotinic acid methyl ester

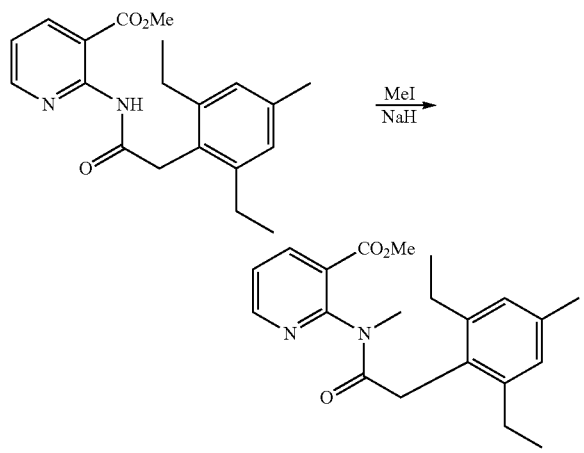

To a solution of 2-[2-(2,6-diethyl-4-methyl-phenyl)-acetylamino]-nicotinic acid methyl ester (Example 1.2) (460 mg) in N,N-dimethylformamide (5 ml) was added iodomethane (0.42 ml) at between −5° C. and 0° C. under a nitrogen atmosphere. The reaction mixture was stirred for 2 minutes before the addition of sodium hydride (60 mg) (60% by weight dispersion in mineral oil) in one portion at between −5° C. and 0° C. The reaction mixture was stirred at between −5° C. and 0° C. for 1 hour, and then at ambient temperature for 2 hours. The reaction mixture was partitioned between diethylether and aqueous hydrochloric acid (2M). The phases were separated and the organic phase was washed with brine, dried over magnesium sulfate and concentrated. The residue was purified by column chromatography on silica gel (eluent: 10% ethyl acetate/dichloromethane) to give 2-{[2-(2,6-diethyl-4-methyl-phenyl)-acetyl]-methyl-amino}-nicotinic acid methyl ester as a light orange oil (370 mg). 1H-NMR (400 MHz, CDCl$_3$): 8.76 (m, 1H), 8.36-8.38 (m, 1H), 7.44-7.47 (m, 1H), 6.83 (s, 2H), 3.97 (s, 3H), 3.33 (bs, 2H), 3.27 (bs, 3H), 2.47-2.57 (m, 4H), 2.26 (bs, 3H), 1.09-1.12 (m, 6H) ppm.

The following compounds made were made using analogous procedures.

2-{[2-(2-Chloro-3,6-difluoro-phenyl)-acetyl]-methyl-amino}-nicotinic acid methyl ester. 1H-NMR (400 MHz, CDCl$_3$): 8.76-8.77 (m, 1H), 8.41-8.44 (m, 1H), 7.49-7.52 (m, 1H), 6.88-7.06 (m, 2H), 3.98 (s, 3H), 3.56 (s, 2H), 3.28 (s, 3H) ppm.

5-Bromo-2-{[2-(2-chloro-3,6-difluoro-phenyl)-acetyl]-methyl-amino}-nicotinic acid methyl ester. The crude compound was used directly for further synthesis.

3-{[2-(2-Chloro-3,6-difluoro-phenyl)-acetyl]-methyl-amino}-pyridine-2-carboxylic acid methyl ester. 1H-NMR (400 MHz, CDCl$_3$): 8.79-8.80 (m, 1H), 7.81-7.83 (m, 1H), 7.63-7.66 (m, 1H), 6.91-7.11 (m, 2H), 4.03 (s, 3H), 3.55-3.59 (m, 2H), 3.28 (s, 3H) ppm.

3-{[2-(2,6-Diethyl-4-methyl-phenyl)-acetyl]-methyl-amino}-pyridine-2-carboxylic acid methyl ester. 1H-NMR (400 MHz, CDCl$_3$): 8.76-8.78 (dd, 1H), 7.71-7.74 (dd, 1H), 7.59-7.62 (m, 1H), 6.82 (s, 2H), 4.03 (s, 3H), 3.67 (s, 2H), 3.26 (s, 3H), 2.45 (q, 4H), 2.26 (s, 3H), 1.11 (t, 6H) ppm.

3-{[2-(2-Chloro-3,6-difluoro-phenyl)-acetyl]-methyl-amino}-isonicotinic acid ethyl ester. 1H-NMR (400 MHz, CDCl$_3$): 8.75-8.76 (d, 1H), 8.69 (d, 1H), 7.82-7.84 (dd, 1H), 6.93-7.03 (m, 1H), 6.85-6.90 (m, 1H), 4.35-4.42 (m, 2H), 3.40 (s, 2H), 3.20 (s, 3H), 1.32-1.36 (t, 3H) ppm.

2-{[2-(2-Chloro-3,6-difluoro-phenyl)-acetyl]-methyl-amino}-6-trifluoromethyl-nicotinic acid methyl ester used crude in the next step Example 3.2

Preparation of 3-(2,6-diethyl-4-methyl-phenyl)-4-hydroxy-1-methyl-1H-[1,8]naphthyridin-2-one (Compound No. D20 of Table D)

To a solution of 2-{[2-(2,6-diethyl-4-methyl-phenyl)-acetyl]-methyl-amino}-nicotinic acid methyl ester (300 mg) in N,N-dimethylformamide (5 ml) was added potassium tert-butoxide (250 mg). The reaction mixture was stirred at ambient temperature for 18 hours, and then at 50° C. for 2 hours. The reaction mixture was partitioned the reaction between water and dichloromethane. The phases were separated and the aqueous phase was extracted with further dichloromethane and ethyl acetate. The aqueous phase was acidified by addition of aqueous hydrochloric acid (2M) and extracted three times with ethyl acetate. The combined organic extracts were dried over magnesium sulfate and concentrated. The residue was passed through a plug of silica eluting with ethyl acetate to give Compound No. D20 of Table D as an off-white solid (320 mg).

The following compounds made were made using analogous procedures:

3-(2,6-Diethyl-4-methyl-phenyl)-4-hydroxy-1-methyl-1H-[1,5]naphthyridin-2-one. 1H-NMR (400 MHz, CDCl$_3$): 8.50-8.51 (m, 1H), 7.76-7.78 (m, 1H), 7.59-7.62 (m, 1H), 7.01 (s, 2H), 3.75 (s, 3H), 2.36 (s, 3H), 2.34-2.46 (m, 4H), 1.09 (t, 6H) ppm.

Compound No. A3 of Table A, Compound No. B4 of Table B, Compound No. C1 of Table C, Compound Nos. D5, D18, D22, D26 and D29 of Table D.

Example 3.3

Preparation of 2,2-dimethyl-propionic acid 6-bromo-3-(2-chloro-3,6-difluoro-phenyl)-1-methyl-2-oxo-1,2-dihydro-[1,8]naphthyridin-4-yl ester (Compound No. D13 of Table D)

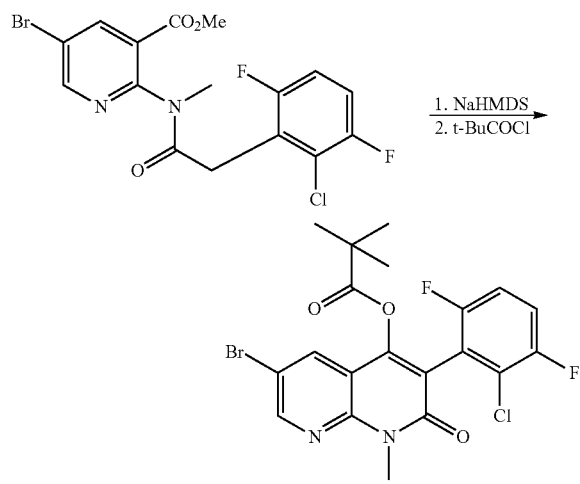

Sodium hexamethyldisilazide ("NaHMDS") (1.78 ml) (1M in tetrahydrofuran) was added dropwise to a solution of 5-bromo-2-{[2-(2-chloro-3,6-difluoro-phenyl)-acetyl]-methyl-amino}-nicotinic acid methyl ester (Example 3.1) (0.22 g) in tetrahydrofuran (5 ml) under a nitrogen atmosphere and heated to 40° C. for 2 hours. 2,2-Dimethyl-propionyl chloride (0.3 ml) was added to the reaction mixture and the reaction mixture heated for a further hour. The reaction mixture was partitioned between dichloromethane and water. The phases were separated and the organic phase was concentated. The residue was purified by column chromatography on silica gel (eluent: ethyl acetate/hexane 1:4) to give Compound No. D13 of Table D as an off-white solid (16 mg).

4. Reactions that are Covered by Scheme 4

Example 4.1

Preparation of 6-chloro-2-methylamino-nicotinic acid methyl ester

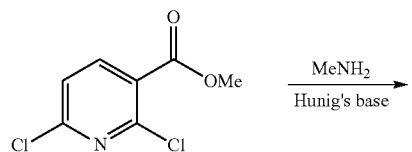

-continued

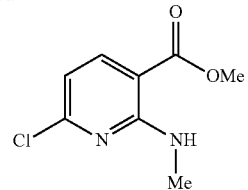

A solution of 2,6-dichloro-nicotinic acid methyl ester (1.5 g), methylamine (0.99 ml) (33% by weight in ethanol) and diisopropylethylamine ("Hunig's base") (1.38 ml) was heated in a microwave for 10 minutes at 120° C. The reaction mixture was partitioned between ethyl acetate and water. The phases were separated and the organic layer was concentrated. The residue was purified by column chromatography on silica gel (eluent: ethyl acetate/hexane 1:9) to give 6-chloro-2-methylamino-nicotinic acid methyl ester as a white solid (915 mg). 1H-NMR (400 MHz, CDCl$_3$): 8.03 (bs, 1H), 7.99-8.01 (d, 1H), 6.49-6.51 (d, 1H), 3.86 (s, 3H), 3.05-3.06 (d, 3H) ppm.

The following compounds made were made using analogous procedures.

2-Chloro-6-methyl-4-methylamino-nicotinic acid ethyl ester. 1H-NMR (400 MHz, CDCl$_3$): 7.16 (bs, 1H), 6.32 (s, 1H), 4.35-4.40 (q, 2H), 2.67-2.89 (d, 3H), 2.41 (s, 3H), 1.38-1.42 (t, 3H) ppm.

4-Chloro-6-methyl-2-methylamino-nicotinic acid ethyl ester 1H-NMR (400 MHz, CDCl$_3$): 7.35 (bs, 1H), 6.46 (s, 1H), 4.35-4.40 (q, 2H), 3.00-3.01 (d, 3H), 2.37 (s, 3H), 1.38-1.42 (t, 3H) ppm.

2-Ethylamino-4-methoxy-nicotinic acid ethyl ester. 1H-NMR (400 MHz, CDCl$_3$): 8.08-8.10 (d, 1H), 7.54 (bs, 1H), 6.15-6.17 (d, 1H), 4.31-4.36 (q, 2H), 3.85 (s, 3H), 3.45-3.52 (m, 2H), 1.35-1.39 (t, 3H), 1.23-1.27 (t, 3H) ppm.

Example 4.2

Preparation of 4-chloro-2-{[2-(2-chloro-3,6-difluoro-phenyl)-acetyl]-methyl-amino}-6-methyl-nicotinic acid ethyl ester

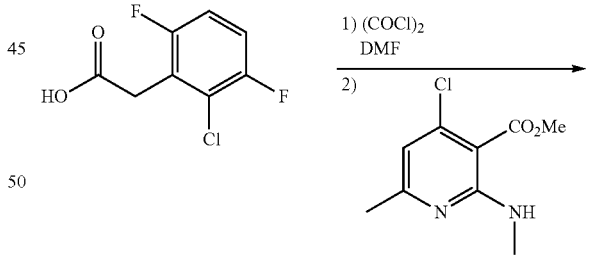

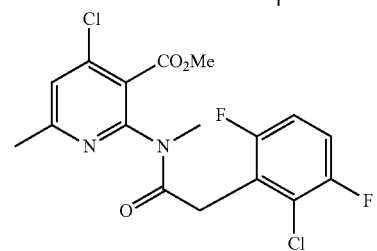

Oxalyl chloride (0.19 ml) was added dropwise to a solution of (2-chloro-3,6-difluoro-phenyl)-acetic acid (373 mg) in dichloromethane (5 ml) at ambient temperature. A drop of N,N-dimethylformamide ("DMF") was added to initiate the reaction. The reaction mixture was stirred at ambient temperature for 1 hour. The reaction mixture was concentrated to give a colourless oil which was dissolved in dichloromethane (5 ml). The mixture was added dropwise to a slurry of 4-chloro-6-methyl-2-methylamino-nicotinic acid ethyl ester (Example 4.1) (413 mg) and pyridine (0.16 ml) in dichloromethane (5 ml). The reaction mixture was stirred at ambient temperature for 16 hours. The reaction mixture was partitioned between dichloromethane and water. The phases were separated and the organic layer was concentrated. The residue was purified by column chromatography on silica gel (eluent: ethyl acetate/hexane 1:4) to give 4-chloro-2-{[2-(2-chloro-3,6-difluoro-phenyl)-acetyl]-methyl-amino}-6-methyl-nicotinic acid ethyl ester as a yellow solid (299 mg). $^1$H NMR (400 MHz, CDCl$_3$): 7.32 (bs, 1H), 7.00-7.05 (m, 1H), 6.90-6.96 (m, 1H), 4.43-4.45 (m, 2H), 3.66 (s, 2H), 3.24 (m, 3H), 2.60 (s, 3H), 1.37-1.40 (t, 3H) ppm.

The following compounds made were made using analogous procedures.

2-Chloro-4-{[2-(2-chloro-3,6-difluoro-phenyl)-acetyl]-methyl-amino}-6-methyl-nicotinic acid ethyl ester. 1H NMR (400 MHz, CDCl$_3$): 7.13 (s, 1H), 7.02-7.08 (m, 1H), 6.93-7.00 (m, 1H), 4.42-4.46 (m, 2H), 3.49-3.75 (m, 2H), 3.21 (s, 3H), 2.64 (s, 3H), 1.38-1.42 (t, 3H) ppm.

6-Chloro-2-{[2-(2-chloro-3,6-difluoro-phenyl)-acetyl]-methyl-amino}-nicotinic acid methyl ester. The crude compound was used directly for further synthesis.

Furthermore, 2-amino-6-trifluoromethyl-nicotinic acid methyl ester can be prepared according to WO 08/076,425 and 2-chloro-4-methoxy-nicotinic acid ethyl ester can be prepared following the method and references in J. Org. Chem., Vol. 70, No. 16, 2005.

TABLE A

Compounds of formula (A), where $R^3$, $R^4$ and $R^5$ have the values as described in the table below.

(A)

| Comp No. | $R^3$ | $R^4$ | $R^5$ | 1H-NMR (400 MHz, CDCl$_3$ except where indicated; chemical shifts in ppm) |
|---|---|---|---|---|
| A1 | H | 2,4-dichloro-phenyl- | HO— | d$_6$-DMSO: 11.68 (bs, 1H), 8.52 (d, 1H), 7.63-7.74 (m, 3H), 7.45-7.48 (dd, 1H), 7.36 (d, 1H). |
| A2 | H | 2-trifluoro-methoxy-phenyl- | HO— | d$_6$-DMSO: 11.64 (bs, 1H), 8.51-8.52 (dd, 1H), 7.71-7.74 (m, 1H), 7.62-7.65 (m, 1H), 7.47-7.51 (m, 1H), 7.41-7.43 (m, 3H). |
| A3 | Me | 2-chloro-3,6-difluoro-phenyl- | HO— | d$_6$-DMSO: 11.79 (bs, 1H), 8.61-8.62 (dd, 1H), 8.10 (dd, 1H), 7.79-7.82 (m, 1H), 7.51-7.57 (m, 1H), 7.35-7.40 (m, 1H), 3.64 (s, 3H). |
| A4 | Me | 2-chloro-3,6-difluoro-phenyl- | i-Pr—(CO)O— | 7.57-7.59 (dd, 1H), 7.78 (dd, 1H), 7.55-7.58 (m, 1H), 7.18-7.24 (m, 1H), 7.05-7.10 (m, 1H), 3.78 (s, 3H), 2.82 (sept, 1H), 1.13-1.16 (dd, 6H). |
| A5 | Me | 2-chloro-3,6-difluoro-phenyl- | t-Bu—(CO)O— | 8.57-8.58 (dd, 1H), 7.75-7.78 (dd, 1H), 7.54-7.57 (m, 1H), 7.17-7.23 (m, 1H), 7.04-7.10 (m, 1H), 3.78 (s, 3H), 1.21 (s, 9H). |
| A6 | Me | 2,6-diethyl-4-methyl-phenyl- | i-Pr—(CO)O— | 8.66-8.67 (dd, 1H), 7.82-7.85 (m, 1H), 7.57-7.61 (m, 1H), 6.97 (s, 2H), 3.79 (s, 3H), 2.71 (sept, 1H), 2.33-2.44 (m, 4H), 2.35 (s, 3H), 1.08-1.12 (m, 6H), 0.93 (bs, 6H). |
| A7 | H | 3-pyridyl- | HO— | d$_6$-DMSO: 11.75 (bs, 1H), 8.73 (m, 1H), 8.52-8.54 (m, 2H), 7.99-8.01 (m, 1H), 7.73-7.75 (m, 1H), 7.63-7.67 (m, 1H), 7.50-7.53 (m, 1H). |
| A8 | H | 2-pyridyl- | HO— | d$_6$-DMSO: 11.13 (bs, 1H), 9.33.-9.35 (m, 1H), 8.59-8.60 (m, 1H), 8.42-8.44 (m, 1H), 8.10-8.14 (m, 1H), 7.58-7.60 (m, 1H), 7.47-7.50 (m, 1H), 7.42-7.46 (m, 1H). |
| A9 | H | 2,4,6-trifluoro-phenyl- | HO— | Described in WO 04/056824 (Compound No. 13 of Table 128 on page 62). |

TABLE B

Compounds of formula (B), where $R^3$, $R^4$ and $R^5$ have the values as described in the table below.

(B)

| Comp No. | $R^{1a}$ | $R^{1b}$ | $R^{1c}$ | $R^3$ | $R^4$ | $R^5$ | 1H-NMR (400 MHz, CDCl$_3$ except where indicated; chemical shifts in ppm) |
|---|---|---|---|---|---|---|---|
| B1 | H | H | H | Et | 2-chloro-3,6-difluoro-phenyl- | t-Bu—(CO)O— | 8.84 (s, 1H), 8.71 (d, 1H), 7.32 (d, 1H), 7.18-7.23 (m, 1H), 7.05-7.10 (m, 1H), 4.38 (q, 2H), 1.41 (t, 3H), 1.16 (s, 9H). |
| B2 | H | H | H | H | 2-chloro-3,6-difluoro-phenyl- | HO— | d$_6$-DMSO: 11.74 (bs, 1H), 8.97 (s, 1H), 8.44-8.45 (d, 1H), 7.39-7.45 (m, 1H), 7.22-7.26 (m, 1H), 7.17-7.19 (d, 1H). |
| B3 | H | H | H | H | 2-chloro-3,6-difluoro-phenyl- | t-Bu—(CO)O— | 8.83 (s, 1H), 8.61-8.63 (d, 1H), 7.23-7.28 (m, 2H), 7.09-7.14 (m, 1H), 1.16 (s, 9H). |
| B4 | Cl | Me | H | Me | 2-chloro-3,6-difluoro-phenyl- | HO— | 7.48 (s, 1H), 7.34-7.40 (m, 1H), 7.18-7.23 (m, 1H), 3.70 (s, 3H), 2.63 (s, 3H). |
| B5 | Cl | Me | H | Me | 2-chloro-3,6-difluoro-phenyl- | t-Bu—(CO)O— | 7.14 (s, 1H), 7.18-7.23 (m, 1H), 7.06-7.10 (m, 1H), 3.76 (s, 3H), 2.66 (s, 3H), 1.03 (s, 9H). |

TABLE C

Compounds of formula (C), where $R^3$, $R^4$ and $R^5$ have the values as described in the table below.

(C)

| Comp No. | $R^3$ | $R^4$ | $R^5$ | 1H-NMR (400 MHz, CDCl$_3$ except where indicated; chemical shifts in ppm) |
|---|---|---|---|---|
| C1 | Me | 2-chloro-3,6-difluoro-phenyl- | HO— | d$_6$-DMSO: 8.76 (s, 1H), 8.34 (d, 1H), 7.82-7.83 (d, 1H), 7.10-7.16 (m, 1H), 6.96-7.00 (m, 1H), 3.63 (s, 3H). |
| C2 | Me | 2-chloro-3,6-difluoro-phenyl- | i-Pr—(CO)O— | 8.97 (s, 1H), 8.55-8.56 (d, 1H), 7.42-7.43 (d, 1H), 7.19-7.25 (m, 1H), 7.05-7.11 (m, 1H), 3.88 (s, 3H), 2.68-2.75 (m, 1H), 1.07-1.10 (d, 6H). |

TABLE C-continued

Compounds of formula (C), where $R^3$, $R^4$ and $R^5$ have the values as described in the table below.

(C)

| Comp No. | $R^3$ | $R^4$ | $R^5$ | 1H-NMR (400 MHz, CDCl₃ except where indicated; chemical shifts in ppm) |
|---|---|---|---|---|
| C3 | H | 2,4,6-trifluorophenyl- | HO— | Described in WO 04/056824 (Compound No. 25 of Table 128 on page 62). |

TABLE D

Compounds of formula (D), where $R^3$, $R^4$ and $R^5$ have the values as described in the table below.

(D)

| Comp No. | $R^{1a}$ | $R^{1b}$ | $R^{1c}$ | $R^3$ | $R^4$ | $R^5$ | 1H-NMR (400 MHz, CDCl₃ except where indicated; chemical shifts in ppm) |
|---|---|---|---|---|---|---|---|
| D1 | H | H | H | H | 2,4-dichlorophenyl- | HO— | d₆-DMSO: 8.54-8.56 (dd, 1H), 8.22-8.29 (dd, 1H), 7.69 (d, 1H), 7.45-7.48 (dd, 1H), 7.34 (d, 1H), 7.25-7.28 (dd, 1H). |
| D2 | H | H | H | H | 2,6-dichlorophenyl- | HO— | d₆-DMSO: 11.92 (bs, 1H), 10.97 (bs, 1H), 8.56-8.58 (dd, 1H), 8.31-8.33 (dd, 1H), 7.55 (d, 1H), 7.53 (s, 1H), 7.48-7.50 (m, 1H), 7.27-7.28 (m, 1H). |
| D3 | H | H | H | H | 2-trifluoromethoxyphenyl- | HO— | d₆-DMSO: 11.84 (bs, 1H), 10.73 (bs, 1H), 8.54-8.55 (dd, 1H), 8.32-8.35 (dd, 1H), 7.49-7.51 (m, 1H), 7.40-7.44 (m, 3H), 7.25-7.28 (m, 1H). |
| D4 | H | H | H | H | 2-chloro-3,6-difluorophenyl- | HO— | d₆-DMSO: 12.01 (bs, 1H), 11.21 (bs, 1H), 8.58-8.60 (dd, 1H), 8.33-8.36 (dd, 1H), 7.51-7.56 (m, 1H), 7.33-7.38 (m, 1H), 7.28-7.31 (m, 1H). |
| D5 | H | H | H | Me | 2-chloro-3,6-difluorophenyl- | HO— | d₆-DMSO: 11.29 (bs, 1H), 8.73-8.75 (dd, 1H), 8.43-8.45 (dd, 1H), 7.52-7.58 (m, 1H), 7.34-7.40 (m, 2H), 3.68 (s, 3H). |
| D6 | H | H | H | Me | 2,6-diethyl-4-methylphenyl- | i-Pr—(CO)O— | 8.65-8.67 (dd, 1H), 7.75-7.78 (dd, 1H), 7.19-7.22 (m, 1H), 6.96 (s, 2H), 3.90 (s, 3H), 2.53 (sept, 1H), 2.30-2.45 (m, 7H), 1.11 (t, 6H), 0.90 (d, 6H). |

TABLE D-continued

Compounds of formula (D), where $R^3$, $R^4$ and $R^5$ have the values as described in the table below.

(D)

| Comp No. | $R^{1a}$ | $R^{1b}$ | $R^{1c}$ | $R^3$ | $R^4$ | $R^5$ | 1H-NMR (400 MHz, CDCl$_3$ except where indicated; chemical shifts in ppm) |
|---|---|---|---|---|---|---|---|
| D7 | H | H | H | Me | 2-chloro-3,6-difluoro-phenyl- | i-Pr—(CO)O- | 8.71-8.73 (dd, 1H), 7.87-7.90 (dd, 1H), 7.17-7.27 (m, 2H), 7.04-7.10 (m, 1H), 3.92 (s, 3H), 2.70 (sept, 1H), 1.06-1.09 (dd, 6H). |
| D8 | H | H | H | Me | 2,6-diethyl-4-methyl-phenyl- | t-Bu—(CO)O— | 8.66-8.67 (dd, 1H), 7.71-7.73 (dd, 1H), 7.19-7.22 (m, 1H), 6.95 (s, 2H), 3.91 (s, 3H), 2.31-2.43 (m, 4H), 2.33 (s, 3H), 1.10 (t, 6H), 0.99 (s, 9H). |
| D9 | H | H | H | Me | 2-chloro-3,6-difluoro-phenyl- | t-Bu—(CO)O— | 8.71-8.73 (dd, 1H), 7.83-7.86 (dd, 1H), 7.24-7.27 (m, 1H), 7.17-7.23 (m, 1H), 7.04-7.09 (m, 1H), 3.92 (s, 3H), 1.15 (t, 9H). |
| D10 | H | H | H | F$_2$HC—H$_2$C— | 2-chloro-3,6-difluoro-phenyl- | t-Bu—(CO)O— | 8.75-8.76 (dd, 1H), 7.91-7.93 (dd, 1H), 7.32-7.37 (m, 1H), 7.23-7.28 (m, 1H), 7.09-7.15 (m, 1H), 6.21-6.50 (tt, 1H), 5.05-5.13 (m, 2H), 1.20 (t, 9H). |
| D11 | H | H | H | H | 3-pyridyl- | HO— | d$_6$-DMSO: 11.75 (bs, 1H), 8.70 (m, 1H), 8.52-8.53 (dd, 1H), 8.48-8.49 (dd, 1H), 8.35-8.37 (dd, 1H), 7.98 (d, 1H), 7.45-7.49 (dd, 1H), 7.23-7.26 (dd, 1H). |
| D12 | H | H | H | H | 2-pyridyl- | HO— | — |
| D13 | H | Br | H | Me | 2-chloro-3,6-difluoro-phenyl- | t-Bu—(CO)O— | 8.72 (d, 1H), 7.89 (d, 1H), 7.18-7.23 (m, 1H), 7.04-7.09 (m, 1H), 3.88 (s, 3H), 1.15 (s, 9H). |
| D14 | H | H | Cl | H | 2-chloro-3,6-difluoro-phenyl- | HO— | d$_4$-MeOH: 8.34-8.36 (d, 1H), 7.30-7.32 (d, 1H), 7.31-7.37 (m, 1H), 7.16-7.21 (m, 1H). |
| D15 | H | H | Cl | H | 2-chloro-3,6-difluoro-phenyl- | t-Bu—(CO)O— | 9.10 (bs, 1H), 7.72-7.75 (d, 1H), 7.24-7.26 (d, 1H), 7.19-7.24 (m, 1H), 7.05-7.10 (m, 1H), 1.14 (s, 9H). |
| D16 | H | H | Cl | Me | 2-chloro-3,6-difluoro-phenyl- | t-Bu—(CO)O— | 7.75-7.77 (d, 1H), 7.23-7.25 (d, 1H), 7.18-7.23 (m, 1H), 7.04-7.09 (m, 1H), 3.88 (s, 3H), 1.14 (s, 9H). |
| D17 | H | H | Cl | F$_2$HC—H$_2$C— | 2-chloro-3,6-difluoro-phenyl- | HO— | 8.43-8.45 (d, 1H), 7.39-7.41 (d, 1H), 7.33-7.39 (m, 1H), 7.17-7.23 (m, 1H), 6.09-6.39 (tt, 1H), 4.81-4.83 (m, 2H). |
| D18 | Cl | H | Me | Me | 2-chloro-3,6-difluoro-phenyl- | HO— | 7.28 (s, 1H), 7.32-7.38 (m, 1H), 7.17-7.22 (m, 1H), 3.79 (s, 3H), 2.60 (s, 3H). |
| D19 | Cl | H | Me | Me | 2-chloro-3,6-difluoro-phenyl- | t-Bu—(CO)O— | 7.11 (s, 1H), 7.17-7.22 (m, 1H), 7.05-7.09 (m, 1H), 3.89 (s, 3H), 2.62 (s, 3H), 1.01 (s, 9H). |

TABLE D-continued

Compounds of formula (D), where $R^3$, $R^4$ and $R^5$ have the values as described in the table below.

(D)

| Comp No. | $R^{1a}$ | $R^{1b}$ | $R^{1c}$ | $R^3$ | $R^4$ | $R^5$ | 1H-NMR (400 MHz, CDCl$_3$ except where indicated; chemical shifts in ppm) |
|---|---|---|---|---|---|---|---|
| D20 | H | H | H | Me | 2,6-diethyl-4-methyl-phenyl- | HO— | 8.65-8.67 (m, 1H), 8.25-8.27 (dd, 1H), 7.19-7.22 (m, 1H), 7.06 (s, 2H), 3.86 (s, 3H), 2.31-2.48 (m, 4H), 2.38 (s, 3H), 1.08 (t, 6H). |
| D21 | H | H | H | F$_2$HC—H$_2$C— | 2-chloro-3,6-difluoro-phenyl- | HO— | 8.72 (d, 1H), 8.40-8.42 (d, 1H), 7.32-7.35 (d, 1H), 7.20-7.24 (m, 1H), 7.09-7.14 (m, 1H), 6.13-6.44 (tt, 1H), 4.94-5.02 (m, 2H). |
| D22 | H | H | Cl | Me | 2-chloro-3,6-difluoro-phenyl- | HO— | d$_4$-MeOH: 8.40-8.43 (d, 1H), 7.35-7.37 (d, 1H), 7.32-7.38 (m, 1H), 7.17-7.22 (m, 1H), 3.75 (s, 3H). |
| D23 | H | H | H | F$_2$HC—H$_2$C— | 3-bromo-2-chloro-6-fluoro-phenyl- | i-Pr—(CO)O— | 8.69 (d, 1H) 7.90-7.91 (d, 1H) 7.66-7.70 (m, 1H) 7.26-7.31 (m, 2H) 7.00-7.04 (m, 1H), 6.15-6.46 (tt, 1H) 4.99-5.07 (m, 2H) 2.67-2.74 (m, 1H) 1.06-1.08 (m, 6H). |
| D24 | H | H | H | Me | 2,4,6-trimethyl-phenyl- | HO— | — |
| D25 | H | H | H | H | 3-methoxy-phenyl- | HO— | — |
| D26 | MeO— | H | H | Et | 2,3-dichloro-6-fluoro-phenyl- | HO— | 9.28 (bs, 1H) 8.59-8.60 (d, 1H), 7.45-7.49 (m, 1H), 7.03-7.07 (m, 1H), 6.79 (d, 1H), 4.58-4.63 (q, 2H) 4.14 (s, 3H), 1.32-1.35 (t, 3H). |
| D27 | H | Br | H | H | 2,6-difluoro-phenyl- | HO— | — |
| D28 | H | Br | H | H | 2,4,6-trifluoro-phenyl- | HO— | — |
| D29 | H | H | F$_3$C— | Me | 2-chloro-3,6-difluoro-phenyl- | HO— | 8.55 (d, 1H), 7.56 (d, 1H), 7.08-7.13 (m, 1H), 6.98-7.03 (m, 1H), 3.81 (s, 3H). |
| D30 | H | H | F$_3$C— | Me | 2-chloro-3,6-difluoro-phenyl- | t-Bu—(CO)O— | 8.01 (d, 1H), 7.60 (d, 1H), 7.20-7.26 (m, 1H), 7.06-7.11 (m, 1H), 3.93 (s, 3H) 1.16 (s, 9H). |
| D31 | H | H | F$_3$C— | H | 2-chloro-3,6-difluoro-phenyl- | t-Bu—(CO)O— | 7.99 (d, 1H), 7.61 (d, 1H), 7.20-7.26 (m, 1H), 7.06-7.11 (m, 1H), 1.16 (s, 9H). |
| D32 | H | H | H | F$_2$HC—H$_2$C— | 3-bromo-2-chloro-6-fluoro-phenyl- | HO— | 8.68-8.69 (d, 1H), 8.36 (d, 1H), 7.66-7.69 (m, 1H), 7.29-7.32 (m, 1H), 7.00-7.05 (m, 1H), 6.09-6.40 (tt, 1H), 4.91-4.99 (m, 2H). |
| D33 | H | H | H | H | 3-bromo-2-chloro-6-fluoro-phenyl- | HO— | d6-DMSO: 11.92 (bs, 1H), 8.53-8.54 (d, 1H), 8.27-8.30 (d, 1H), 7.81-7.84 (m, 1H), 7.22-7.28 (m, 2H). |

TABLE E

Compounds of formula (E), where $A^1, A^2, A^3, A^4, R^3, R^4$ and $R^5$ have the values as described in the table below.

$$\text{(E)}$$

| Comp No. | $A^1$ | $A^2$ | $A^3$ | $A^4$ | $R^3$ | $R^4$ | $R^5$ | 1H-NMR (400 MHz, CDCl$_3$ except where indicated; chemical shifts in ppm) |
|---|---|---|---|---|---|---|---|---|
| E1 | —CH— | N | —CH— | N | H | 2-chloro-3,6-difluoro-phenyl- | t-Bu—(CO)O— | d$_6$-DMSO: 13.29 (bs, 1H), 9.16 (s, 1H), 8.99 (s, 1H), 7.63-7.68 (m, 1H), 7.44-7.50 (m, 1H), 1.07 (s, 9H). |
| E2 | —CH— | N | —CH— | N | Et | 2-chloro-3,6-difluoro-phenyl- | i-Pr—(CO)O— | 9.20 (s, 1H), 8.99 (s, 1H), 7.24-7.29 (m, 1H), 7.10-7.15 (m, 1H), 4.59-4.65 (q, 2H), 2.76 (sept, 1H), 1.43 (t, 3H), 1.14 (d, 3H), 1.12 (d, 3H). |
| E3 | —CH— | N | —CH— | N | F$_2$HC—H$_2$C— | 2-chloro-3,6-difluoro-phenyl- | i-Pr—(CO)O— | 9.22 (s, 1H), 8.94 (s, 1H), 7.26-7.31 (m, 1H), 7.11-7.16 (m, 1H), 6.15-6.45 (tt, 1H), 4.96-5.04 (m, 2H), 2.78 (sept, 1H), 1.12-1.15 (m, 6H). |
| E4 | N | —CH— | N | N | H | 2-chloro-3,6-difluoro-phenyl- | HO— | d$_6$-DMSO: 12.96 (bs, 1H), 9.77 (s, 1H), 7.56-7.62 (m, 1H), 7.38-7.44 (m, 1H). |
| E5 | N | —CH— | N | N | H | 2-chloro-3,6-difluoro-phenyl- | Me—(CO)O— | 9.70 (s, 1H), 9.54 (m, 1H), 7.28-7.33 (m, 1H), 7.11-7.16 (m, 1H), 2.32 (s, 3H). |
| E6 | N | —CH— | N | N | Me | 2-chloro-3,6-difluoro-phenyl- | Me—(CO)O— | 9.69 (s, 1H), 9.54 (m, 1H), 7.26-7.32 (m, 1H), 7.11-7.16 (m, 1H), 4.03 (s, 3H), 2.32 (s, 3H). |
| E7 | N | —CH— | N | N | H | 2-chloro-6-fluoro-phenyl- | HO— | Described in WO 04/056829 (Compound No. 18 of Table 132 on page 64). |
| E8 | —CH— | —CH— | N | N | H | 2-chloro-6-fluoro-phenyl | HO— | Described in WO 04/056825 (Compound No. 42 of Table 129 on page 61). |
| E9 | N | —CH— | N | N | H | 2,4,6-trimethyl-phenyl- | EtO—(CO)O— | 9.68 (s, 1H), 6.96 (s, 2H), 4.20-4.27 (q, 2H), 2.33 (s, 3H), 2.12 (s, 6H), 1.29 (t, 3H). |
| E10 | —CH— | N | —CH— | N | H | 2,4,6-trifluoro-phenyl- | HO— | Described in WO 04/056826 (Compound No. 13 of Table 128 on page 62). |
| E11 | N | —CH— | N | N | H | 2,4,6-trifluoro-phenyl- | HO— | Described in WO 04/056829 (Compound No. 13 of Table 132 on page 64). |

TABLE E-continued

Compounds of formula (E), where $A^1, A^2, A^3, A^4, R^3, R^4$ and $R^5$ have the values as described in the table below.

(E)

| Comp No. | $A^1$ | $A^2$ | $A^3$ | $A^4$ | $R^3$ | $R^4$ | $R^5$ | 1H-NMR (400 MHz, CDCl$_3$ except where indicated; chemical shifts in ppm) |
|---|---|---|---|---|---|---|---|---|
| E12 | N | —CH— | N | N | H | 2,4,6-trimethyl-phenyl- | HO— | 9.59 (s, 1H), 6.97 (s, 2H), 2.34 (s, 3H), 2.31 (s, 6H). |
| E13 | —CH— | N | N | —CH— | H | 2,4,6-trifluoro-phenyl- | HO— | Described in WO 04/056825 (Compound No. 25 of Table 129 on page 61). |

Biological Examples

Example B1

Herbicidal Action

Seeds of a variety of test species were sown in sterilised standard soil in seed trays each having 96 cells. After cultivation for 8 to 9 days cultivation (post-emergence) under controlled conditions in a climatic chamber (cultivation at 23/17° C., day/night; 13 hours light; 50-60% humidity), the plants were treated with an aqueous spray solution of 1000 mg/l of the active ingredient dissolved in 10% DMSO (dimethyl sulfoxide, CAS RN 67-68-5) as a solvent, equivalent to 1000 g/ha. The plants were grown in the climatic chamber after application at (24/19° C., day/night; 13 hours light; 50-60% humidity) and watered twice daily. After 9 days until the test was evaluated (10=total damage to plant, 0=no damage to plant)

TABLE B1

Application post-emergence

| Comp No. | Rate (g/ha) | STEME | NAAOF | AMARE | SOLNI |
|---|---|---|---|---|---|
| A1 | 1000 | 0 | 2 | 0 | 0 |
| A2 | 1000 | 3 | 0 | 0 | 0 |
| A3 | 1000 | 3 | 4 | 6 | 3 |
| A4 | 1000 | 4 | 6 | 5 | 4 |
| A5 | 1000 | 0 | 3 | 0 | 7 |
| A6 | 1000 | 8 | 6 | 3 | 6 |
| A7 | 1000 | 6 | 2 | 0 | 0 |
| D5 | 1000 | 7 | 6 | 7 | 0 |
| D6 | 1000 | 2 | 0 | 0 | 0 |
| D7 | 1000 | 3 | 0 | 6 | 0 |
| D8 | 1000 | 2 | 3 | 0 | 0 |
| D9 | 1000 | 2 | 2 | 3 | 0 |
| D20 | 1000 | 5 | 5 | 0 | 0 |
| E4 | 1000 | 0 | 0 | 2 | 4 |
| E6 | 1000 | 2 | 0 | 0 | 0 |

STEME = *Stellaria media*; NAAOF = *Nasturtium officinale*; AMARE = *Amaranthus retroflexus*; SOLNI = *Solanum nigrum*.

Compound Nos. A8 and A9 of Table A, Compound Nos. B2 and B3 of Table B, Compound No. C3 of Table C, Compound Nos. D1, D2, D3, D4, D11, D12, D15, D25, D27 and D28 of Table D, Compound Nos. E5, E7, E8, E10, E11 and E13 of Table E were tested using the same protocol and showed little or no damage to the test plants under the test conditions.

Example B2

Herbicidal Action

Seeds of a variety of test species were sown in standard soil in pots. After 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days, the test was evaluated (10=total damage to plant; 0=no damage to plant).

TABLE B2

Application post-emergence

| Comp No. | Rate (g/ha) | SOLNI | AMARE | SETFA | ECHCG | IPOHE |
|---|---|---|---|---|---|---|
| B4 | 1000 | 2 | 0 | 0 | 0 | 2 |
| C1 | 1000 | 0 | 0 | 0 | 0 | 2 |
| C2 | 1000 | 2 | 3 | 0 | 0 | 5 |
| D10 | 1000 | 7 | 7 | 0 | 0 | 6 |
| D14 | 1000 | 0 | 4 | 0 | 4 | 0 |
| D16 | 1000 | 2 | 2 | 0 | 0 | 2 |
| D17 | 1000 | 6 | 6 | 0 | 0 | 5 |
| D18 | 1000 | 3 | 2 | 2 | 0 | 0 |
| D21 | 1000 | 10 | 10 | 1 | 2 | 9 |
| D22 | 1000 | 4 | 2 | 0 | 1 | 6 |
| D23 | 1000 | 9 | 4 | 0 | 1 | 4 |
| D24 | 1000 | 1 | 0 | 0 | 0 | 1 |
| D26 | 1000 | 6 | 6 | 4 | 4 | 6 |

TABLE B2-continued

Application post-emergence

| Comp No. | Rate (g/ha) | SOLNI | AMARE | SETFA | ECHCG | IPOHE |
|---|---|---|---|---|---|---|
| D29 | 1000 | 4 | 6 | 0 | 0 | 7 |
| D30 | 1000 | 2 | 0 | 0 | 0 | 2 |
| D31 | 1000 | 0 | 0 | 0 | 0 | 1 |
| D32 | 1000 | 7 | 4 | 1 | 1 | 6 |
| D33 | 1000 | 3 | 1 | 0 | 0 | 7 |
| E2 | 1000 | 4 | 5 | 0 | 2 | 2 |
| E3 | 1000 | 5 | 7 | 0 | 0 | 1 |
| E9 | 1000 | 0 | 0 | 9 | 10 | 1 |
| E12 | 1000 | 1 | 5 | 10 | 10 | 3 |

SOLNI = *Solanum nigrum*; AMARE = *Amaranthus retroflexus*; SETFA = *Setaria faberi*; ECHCG = *Echinochloa crus-galli*; IPOHE = *Ipomea hederaceae*.

Compound Nos. B1 and B5 of Table B, Compound Nos. D13 and D19 of Table D, and Compound No. E1 of Table E were tested using the same protocol and showed little or no damage to the test plants under the test conditions.

The invention claimed is:

1. A method of controlling plants which comprises applying to the plants or to the locus thereof a herbicidally effective amount of a compound of formula (I)

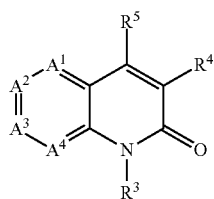

(I)

wherein
$A^1$, $A^2$ and $A^3$ are C—$R^1$ and $A^4$ is N,
each $R^1$ is independently hydrogen, $C_1$-$C_4$alkyl, $C_1$-$C_4$haloalkyl, halo, cyano, hydroxy, $C_1$-$C_4$alkoxy, $C_1$-$C_4$alkylthio, aryl or aryl substituted by one to five $R^6$, which may be the same or different, or heteroaryl or heteroaryl substituted by one to five $R^6$, which may be the same or different;
$R^3$ is hydrogen, $C_1$-$C_{10}$ alkyl, $C_1$-$C_4$haloalkyl, $C_2$-$C_{10}$ alkenyl, $C_2$-$C_4$haloalkenyl, $C_2$-$C_{10}$ alkynyl, $C_2$-$C_4$haloalkynyl, $C_3$-$C_{10}$ cycloalkyl, $C_3$-$C_{10}$ cycloalkyl-$C_1$-$C_6$alkyl-, $C_1$-$C_{10}$alkoxy-$C_1$-$C_6$alkyl-, $C_1$-$C_{10}$cyanoalkyl-, $C_1$-$C_{10}$alkoxycarbonyl-$C_1$-$C_6$alkyl-, N—$C_1$-$C_3$alkyl-aminocarbonyl-$C_1$-$C_6$alkyl-, N,N-di-($C_1$-$C_3$alkyl)-aminocarbonyl-$C_1$-$C_6$alkyl-, aryl-$C_1$-$C_6$alkyl- or aryl-$C_1$-$C_6$alkyl- wherein the aryl moiety is substituted by one to three $R^7$, which may be the same or different, or heterocyclyl-$C_1$-$C_6$alkyl- or heterocyclyl-$C_1$-$C_6$alkyl- wherein the heterocyclyl moiety is substituted by one to three $R^7$, which may be the same or different;
$R^4$ is aryl or aryl substituted by one to five $R^8$, which may be the same or different, or heteroaryl or heteroaryl substituted by one to four $R^8$, which may be the same or different;
$R^5$ is hydroxy or a group which can be metabolised to a hydroxy group;
each $R^6$, $R^7$ and $R^8$ is independently halo, cyano, nitro, $C_1$-$C_{10}$ alkyl, $C_1$-$C_4$haloalkyl, $C_2$-$C_{10}$alkenyl, $C_2$-$C_{10}$alkynyl, hydroxy, $C_1$-$C_{10}$alkoxy, $C_1$-$C_4$haloalkoxy, $C_1$-$C_{10}$alkoxy-$C_1$-$C_4$alkyl-, $C_3$-$C_7$cycloalkyl, $C_3$-$C_7$cycloalkoxy, $C_3$-$C_7$cycloalkyl-$C_1$-$C_4$alkyl-, $C_3$-$C_7$cycloalkyl-$C_1$-$C_4$alkoxy-, $C_1$-$C_6$alkylcarbonyl-, formyl, $C_1$-$C_4$alkoxycarbonyl-, $C_1$-$C_4$alkylcarbonyloxy-, $C_1$-$C_{10}$alkylthio-, $C_1$-$C_4$haloalkylthio-, $C_1$-$C_{10}$alkylsulfinyl-, $C_1$-$C_4$haloalkylsulfinyl-, $C_1$-$C_{10}$alkylsulfonyl-, $C_1$-$C_4$haloalkylsulfonyl-, amino, $C_1$-$C_{10}$alkylamino-, di-$C_1$-$C_{10}$ alkylamino-, $C_1$-$C_{10}$alkylcarbonylamino-, aryl or aryl substituted by one to three $R^{13}$, which may be the same or different, heteroaryl or heteroaryl substituted by one to three $R^{13}$, which may be the same or different, aryl-$C_1$-$C_4$alkyl- or aryl-$C_1$-$C_4$alkyl- wherein the aryl moiety is substituted by one to three $R^{13}$, which may be the same or different, heteroaryl-$C_1$-$C_4$alkyl- or heteroaryl-$C_1$-$C_4$alkyl- wherein the heteroaryl moiety is substituted by one to three $R^{13}$, which may be the same or different, aryloxy- or aryloxy- substituted by one to three $R^{13}$, which may be the same or different, heteroaryloxy- or heteroaryloxy- substituted by one to three $R^{13}$, which may be the same or different, arylthio- or arylthio- substituted by one to three $R^{13}$, which may be the same or different, or heteroarylthio- or heteroarylthio- substituted by one to three $R^{13}$, which may be the same or different; and
each $R^{13}$ is independently halo, cyano, nitro, $C_1$-$C_6$alkyl, $C_1$-$C_6$haloalkyl or $C_1$-$C_6$alkoxy;
or a salt or N-oxide thereof.

2. A method according to claim 1 wherein each $R^1$ is hydrogen, $C_1$-$C_4$alkyl, $C_1$-$C_4$haloalkyl, halo, cyano, hydroxy or $C_1$-$C_4$alkoxy.

3. A method according to claim 1 wherein $R^3$ is hydrogen, $C_1$-$C_4$alkyl, $C_1$-$C_4$haloalkyl, $C_2$-$C_4$alkenyl, $C_2$-$C_4$haloalkenyl, $C_2$-$C_4$alkynyl or $C_2$-$C_4$haloalkynyl.

4. A method according to claim 1 wherein $R^4$ is aryl or aryl substituted by one to five $R^8$, which may be the same or different, and wherein the $R^4$ aryl group is phenyl.

5. A method according to claim 1 wherein $R^5$ is hydroxy, $R^9$-oxy-, $R^{10}$-carbonyloxy-, tri-$R^{11}$-silyloxy- or $R^{12}$-sulfonyloxy-, wherein
$R^9$ is $C_1$-$C_{10}$alkyl, $C_2$-$C_{10}$ alkenyl, $C_2$-$C_{10}$alkynyl or aryl-$C_1$-$C_4$alkyl- or aryl-$C_1$-$C_4$alkyl- wherein the aryl moiety is substituted by one to five substituents independently selected from halo, cyano, nitro, $C_1$-$C_6$alkyl, $C_1$-$C_6$haloalkyl or $C_1$-$C_6$alkoxy;
$R^{10}$ is $C_1$-$C_{10}$alkyl, $C_3$-$C_{10}$cycloalkyl, $C_3$-$C_{10}$cycloalkyl-$C_1$-$C_{10}$alkyl-, $C_1$-$C_{10}$ haloalkyl, $C_2$-$C_{10}$alkenyl, $C_2$-$C_{10}$alkynyl, $C_1$-$C_4$alkoxy-$C_1$-$C_{10}$alkyl-, $C_1$-$C_4$alkylthio-$C_1$-$C_4$alkyl-, $C_1$-$C_{10}$alkoxy, $C_2$-$C_{10}$alkenyloxy, $C_2$-$C_{10}$alkynyloxy, $C_1$-$C_{10}$alkylthio-, N—$C_1$-$C_4$alkyl-amino-, N,N-di-($C_1$-$C_4$alkyl)-amino-, aryl or aryl substituted by one to three $R^{14}$, which may be the same or different, heteroaryl or heteroaryl substituted by one to three $R^{14}$, which may be the same or different, aryl-$C_1$-$C_4$alkyl- or aryl-$C_1$-$C_4$alkyl- wherein the aryl moiety is substituted by one to three $R^{14}$, which may be the same or different, heteroaryl-$C_1$-$C_4$alkyl- or heteroaryl-$C_1$-$C_4$alkyl- wherein the heteroaryl moiety is substituted by one to three $R^{14}$, which may be the same or different, aryloxy- or aryloxy- substituted by one to three $R^{14}$, which may be the same or different, heteroaryloxy- or heteroaryloxy-substituted by one to three $R^{14}$, which may be the same or different, arylthio- or arylthio-substituted by one to three $R^{14}$, which may be the same or different, or heteroarylthio- or heteroarylthio- substituted by one to three $R^{14}$, which may be the same or different;

each $R^{11}$ is independently $C_1$-$C_{10}$alkyl or phenyl or phenyl substituted by one to five substituents independently selected from halo, cyano, nitro, $C_1$-$C_6$alkyl, $C_1$-$C_6$haloalkyl or $C_1$-$C_6$alkoxy;

$R^{12}$ is $C_1$-$C_{10}$alkyl, $C_1$-$C_{10}$ haloalkyl, or phenyl or phenyl substituted by one to five substituents independently selected from halo, cyano, nitro, $C_1$-$C_6$alkyl, $C_1$-$C_6$haloalkyl or $C_1$-$C_6$alkoxy; and each $R^{14}$ is independently halo, cyano, nitro, $C_1$-$C_{10}$alkyl, $C_1$-$C_4$haloalkyl, $C_1$-$C_{10}$alkoxy, $C_1$-$C_4$alkoxycarbonyl-, $C_1$-$C_4$haloalkoxy, $C_1$-$C_{10}$ alkylthio-, $C_1$-$C_4$haloalkylthio-, $C_1$-$C_{10}$alkylsulfinyl-, $C_1$-$C_4$haloalkylsulfinyl-, $C_1$-$C_{10}$ alkylsulfonyl-, $C_1$-$C_4$haloalkylsulfonyl-, aryl or aryl substituted by one to five substituents independently selected from halo, cyano, nitro, $C_1$-$C_6$alkyl, $C_1$-$C_6$haloalkyl or $C_1$-$C_6$alkoxy, or heteroaryl or heteroaryl substituted by one to four substituents independently selected from halo, cyano, nitro, $C_1$-$C_6$alkyl, $C_1$-$C_6$haloalkyl or $C_1$-$C_6$alkoxy.

\* \* \* \* \*